United States Patent
Hergenrother et al.

(10) Patent No.: US 9,592,229 B2
(45) Date of Patent: Mar. 14, 2017

(54) POTENT ANTICANCER ACTIVITY VIA DUAL COMPOUND ACTIVATION

(71) Applicants: The Board of Trustees of the University of Illinois, Urbana, IL (US); Vanquish Oncology, Inc., Champaign, IL (US)

(72) Inventors: Paul J. Hergenrother, Champaign, IL (US); Rachel C. Botham, Champaign, IL (US); Timothy M. Fan, Mahomet, IL (US); Mark J. Gilbert, Seattle, WA (US); Michael K. Handley, Windsor, CO (US); Theodore M. Tarasow, San Ramon, CA (US)

(73) Assignees: The Board of Trustees of the University of Illinois, Urbana, IL (US); Vanquish Oncology, Inc., Champaign, IL (US)

( * ) Notice: Subject to any disclaimer, the term of this patent is extended or adjusted under 35 U.S.C. 154(b) by 164 days.

(21) Appl. No.: 14/382,546

(22) PCT Filed: Mar. 4, 2013

(86) PCT No.: PCT/US2013/028880
§ 371 (c)(1),
(2) Date: Sep. 2, 2014

(87) PCT Pub. No.: WO2013/131089
PCT Pub. Date: Sep. 6, 2013

(65) Prior Publication Data
US 2015/0099759 A1    Apr. 9, 2015

Related U.S. Application Data

(60) Provisional application No. 61/605,819, filed on Mar. 2, 2012.

(51) Int. Cl.
| | | |
|---|---|---|
| *A61K 31/495* | (2006.01) | |
| *A61K 31/437* | (2006.01) | |
| *A61K 47/40* | (2006.01) | |
| *A61K 9/00* | (2006.01) | |
| *A61K 9/20* | (2006.01) | |
| *A61K 9/48* | (2006.01) | |

(52) U.S. Cl.
CPC .......... *A61K 31/495* (2013.01); *A61K 31/437* (2013.01); *A61K 47/40* (2013.01); *A61K 9/008* (2013.01); *A61K 9/0019* (2013.01); *A61K 9/2054* (2013.01); *A61K 9/4858* (2013.01)

(58) Field of Classification Search
None
See application file for complete search history.

(56) References Cited

U.S. PATENT DOCUMENTS

| | | |
|---|---|---|
| 6,303,329 B1 | 10/2001 | Heinrikson et al. |
| 6,403,765 B1 | 6/2002 | Alnemri |
| 6,534,267 B1 | 3/2003 | Wang et al. |
| 6,762,045 B2 | 7/2004 | Krebs et al. |
| 6,878,743 B2 | 4/2005 | Choong et al. |
| 7,041,784 B2 | 5/2006 | Wang et al. |
| 7,632,972 B2 | 12/2009 | Hergenrother et al. |
| 8,592,584 B2 | 11/2013 | Hergenrother et al. |
| 2004/0180828 A1 | 9/2004 | Shi |
| 2007/0049602 A1 | 3/2007 | Hergenrother et al. |
| 2010/0291214 A1 | 11/2010 | Gabriele et al. |
| 2011/0257398 A1 | 10/2011 | Hergenrother et al. |
| 2012/0040995 A1 | 2/2012 | Hergenrother et al. |

FOREIGN PATENT DOCUMENTS

| | | |
|---|---|---|
| RU | 2410389 C2 | 9/2006 |
| RU | 2439695 C2 | 11/2006 |
| RU | 2360692 C1 | 12/2007 |
| RU | 2408584 C2 | 1/2011 |
| WO | 2008134474 A2 | 11/2008 |
| WO | 2009089508 A1 | 7/2009 |

OTHER PUBLICATIONS

Debernard, Karen A. Boldingh. Cell death induced by novel procaspase-3 activators can be reduced by growth factors. Biochemical and Biophysical Research Communications. 413 (2011) 364-369.*
Peterson et al., "Discovery and Canine Preclinical Assessment of a Nontoxic Procaspase-3-Activating Compound," Cancer Research, Sep. 15, 2010. 70: pp. 7232-7241.
Peterson et al., "PAC-1 Activates Procaspase-3 in Vitro through Relief of Zinc-Mediated Inhibition," J. Mol. Biol., Mar. 10, 2009. 388: pp. 144-158.
Peterson et al., "Procaspase-3 Activation as an Anti-Cancer Strategy: Structure- Activity Relationship of Procaspase-Activating Compound 1 (PAC-1) and Its Cellular Co-Localization with Caspase-3," J. Med. Chem., Aug. 8, 2009. 59: pp. 5721-5731.
Putt et al., "Small-molecule activation of procaspase-3 to caspase-3 as a personalized anticancer strategy," Nat Chem. Biol., Oct. 2006. 2: pp. 543-550.

(Continued)

*Primary Examiner* — Samantha Shterengarts

(74) *Attorney, Agent, or Firm* — Haukaas Fortius PLLC; Michael H. Haukaas

(57) ABSTRACT

The invention provides compositions and methods for the induction of cell death, for example, cancer cell death. Combinations of compounds and related methods the use are disclosed, including the use of compounds in therapy for the treatment of cancer and selective induction of apoptosis in cells. The disclosed drug combinations can have lower neurotoxicity effects than other compounds and combinations of compounds.

21 Claims, 16 Drawing Sheets

(56) References Cited

OTHER PUBLICATIONS

Wolan et al., "Small-Molecule Activators of a Proenzyme," Science Mag, 2009. 326: pp. 852-858.
Zorn et al., "Self-Assembling Small Molecules Form Nanofibrils That Bind Procaspase-3 to Promote Activatoin," J. of the American Chem. Soc., Nov. 8, 2011., 133: pp. 19630-19633.
International Search Report and Written Opinion for PCT/US2013/028880, dated Mar. 4, 2013, 3 pp.

* cited by examiner

B)
U-937

A549

BT-549

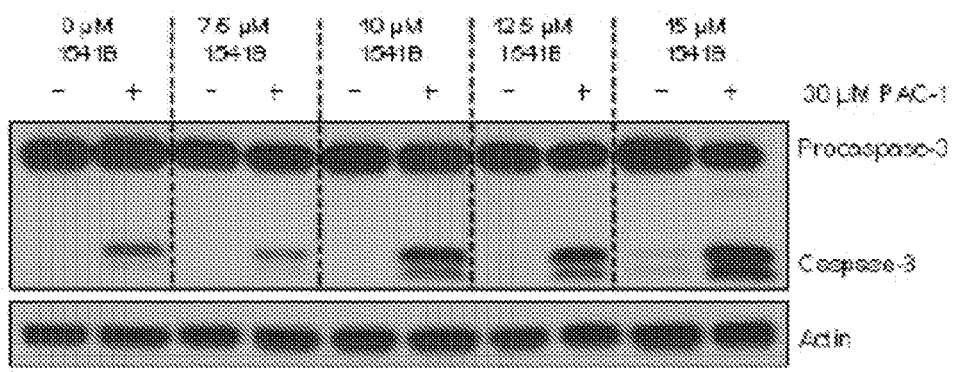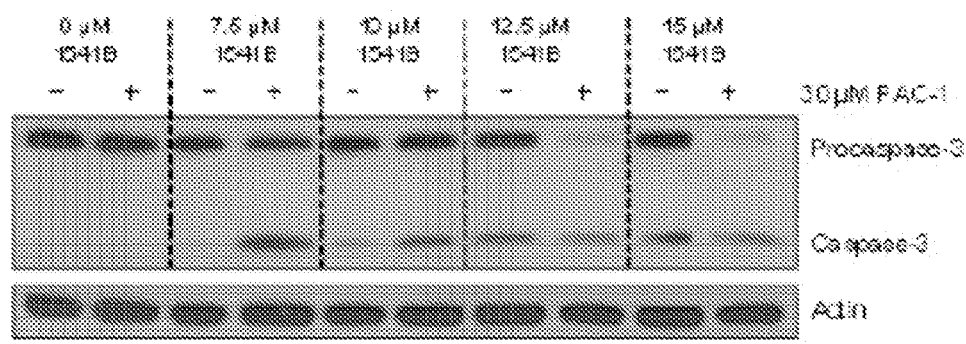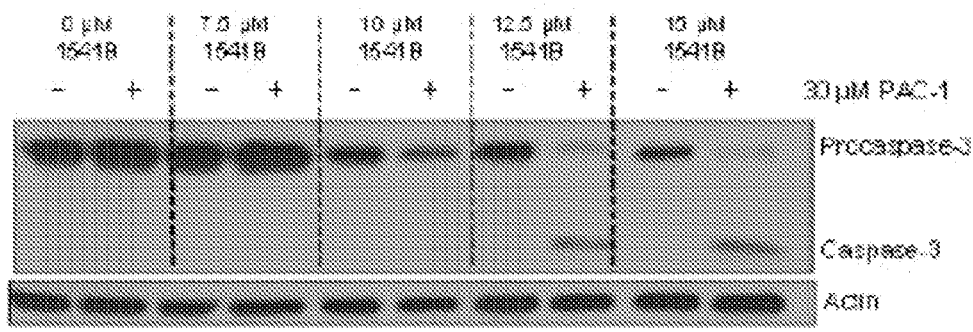
*Figure 6A-C*

Jurkat:

EL4:

HL-60:

A549:

BT549:

A.)

B.)

POTENT ANTICANCER ACTIVITY VIA DUAL COMPOUND ACTIVATION

RELATED APPLICATIONS

This application claims priority under 35 U.S.C. §119(e) to U.S. Provisional Patent Application No. 61/605,819, filed Mar. 2, 2012, which is incorporated herein by reference.

GOVERNMENT SUPPORT

This invention was made with government support under Grant Nos. R01-CA120439 and CA120439-52 awarded by the National Institutes of Health. The government has certain rights in the invention.

BACKGROUND OF THE INVENTION

Apoptosis, or programmed cell death, plays a central role in the development and homeostasis of all multicellular organisms. A frequent hallmark of cancer is resistance to natural apoptotic signals. Depending on the cancer type, this resistance is typically due to up- or down-regulation of key proteins in the apoptotic cascade or to mutations in genes encoding these proteins. Such changes occur in both the intrinsic apoptotic pathway, which funnels through the mitochondria and caspase-9, and the extrinsic apoptotic pathway, which involves the action of death receptors and caspase-8. For example, alterations in proper levels of proteins such as p53, Bim, Bax, Apaf-1, FLIP and many others have been observed in cancers. The alterations can lead to a defective apoptotic cascade, one in which the upstream pro-apoptotic signal is not adequately transmitted to activate the executioner caspases, caspase-3 and caspase-7.

As most apoptotic pathways ultimately involve the activation of procaspase-3, upstream genetic abnormalities are effectively "breaks" in the apoptotic circuitry, and as a result such cells proliferate atypically. Given the central role of apoptosis in cancer, efforts have been made to develop therapeutics that target specific proteins in the apoptotic cascade. For instance, peptidic or small molecule binders to cascade members such as p53 and proteins in the Bcl family or to the inhibitor of apoptosis (IAP) family of proteins have pro-apoptotic activity, as do compounds that promote the oligomerization of Apaf-1. However, because such compounds target early (or intermediate to high) positions on the apoptotic cascade, cancers with mutations in proteins downstream of those members can still be resistant to the possible beneficial effects of those compounds.

It would be advantageous for therapeutic purposes to identify small molecules that directly activate a proapoptotic protein far downstream in the apoptotic cascade. This approach could involve a relatively low position in the cascade, thus enabling the killing of even those cells that have mutations in their upstream apoptotic machinery. Moreover, such therapeutic strategies would have a higher likelihood of success if that proapoptotic protein were upregulated in cancer cells. Thus, the identity small molecules that target the downstream effector protein of apoptosis, procaspase-3, would significantly aid current cancer therapy.

The conversion or activation of procaspase-3 to caspase-3 results in the generation of the active "executioner" caspase form that subsequently catalyzes the hydrolysis of a multitude of protein substrates. Active caspase-3 is a homodimer of heterodimers and is produced by proteolysis of procaspase-3. In vivo, this proteolytic activation typically occurs through the action of caspase-8 or caspase-9. To ensure that the zymogen (proenzyme) is not prematurely activated, procaspase-3 has a 12 amino acid "safety catch" that blocks access to the ETD site (amino acid sequence, ile-glu-thr-asp) of proteolysis. This safety catch enables procaspase-3 to resist autocatalytic activation and proteolysis by caspase-9. Mutagenic studies indicate that three consecutive aspartic acid residues appear to be the critical components of the safety catch. The position of the safety catch is sensitive to pH, thus upon cellular acidification (as occurs during apoptosis) the safety catch is thought to allow access to the site of proteolysis, and active caspase-3 can be produced either by the action of caspase-9 or through an autoactivation mechanism.

In certain cancers, the levels of procaspase-3 are elevated relative to normal tissue. A study of primary isolates from 20 colon cancer patients revealed that on average, procaspase-3 was upregulated six-fold in such isolates relative to adjacent non-cancerous tissue. In addition, procaspase-3 is upregulated in certain neuroblastomas, lymphomas, and liver cancers. Furthermore, a systematic evaluation was performed of procaspase-3 levels in the 60 cell-line panel used for cancer screening by the National Cancer Institute (NCI) Developmental Therapeutics Program, which revealed that certain lung, melanoma, renal, and breast cancers show greatly enhanced levels of procaspase-3 expression.

Due to the role of active caspase-3 in achieving apoptosis, the relatively high levels of procaspase-3 in certain cancerous cell types, and the intriguing safety catch-mediated suppression of its autoactivation, small molecules that directly modify procaspase-3 could have great applicability in targeted cancer therapy.

Combination therapy has become standard for treatment of cancer patients. The goal of combination therapy drug cocktail regimes is to achieve a synergistic or additive effect between chemotherapeutics, thereby facilitating shortened treatment times, decreased toxicity, and increased patient survival. Drugs that act on a single biochemical pathway are particularly strong candidates for synergy or potentiation as they may mimic "synthetic lethal" genetic combinations. For example, inhibitors of poly(ADP-ribose)polymerase-1 (PARP-1), an enzyme that facilitates DNA damage repair, potently synergize with DNA damaging agents as demonstrated in cell culture, animal models, and human clinical trials. However, there is still a need for more effective therapies for the treatment of many forms of cancer, and new synergistic combinations of anticancer drugs would aid this pursuit. Accordingly, there exists a need to identify new cytotoxic agents that are effective in killing cancer cells yet protect normal host tissues from the undesired toxicity of the cytotoxic agent.

SUMMARY

The invention broadly provides compounds, compositions, and methods of therapeutic treatment. In embodiments, the inventions are applicable in the context of a variety of cancer diseases and cancer cell types such as breast, lymphoma, adrenal, renal, melanoma, leukemia, neuroblastoma, lung, brain, and others known in the art. Herein is disclosed, inter alia, compositions and methods including small molecules capable of inducing cell death. In various embodiments, the compositions and methods involve compounds that can interact directly or indirectly with programmed cell death pathway members such as procaspase-3. In some embodiments, the compositions and methods have reduced neurotoxicity compared to other compounds that interact directly or indirectly with programmed cell death pathway members such as procaspase-3.

Combination anticancer therapy can consist of drugs that target different biochemical pathways, or those that hit different targets in the same pathway, mimicking "synthetic lethal" genetic combinations. This disclosure demonstrates a new concept in combination therapy, that of enzyme activation with two compounds that selectively activate the same biological target, but through different mechanisms. Combinations of the procaspase-3 activators PAC-1 and 1541B show considerable synergy in the activation of procaspase-3 enzymatic activity in vitro, induce rapid and dramatic automaturation of procaspase-3 in multiple cancer cell lines in culture, and powerfully induce apoptotic death of cancer cells in culture to a degree well exceeding the additive effect. Finally, the combination of PAC-1 and 1541B effectively reduces tumor burden in a murine tumor model in which the compounds alone have minimal or no effect. These data indicate the potential of PAC-1/1541B combinations for the treatment of cancer and, more broadly, show that differentially acting enzyme activators can synergize to provide a significantly heightened biological effect.

Accordingly, the invention provides a composition comprising (a) a compound of Formula (I):

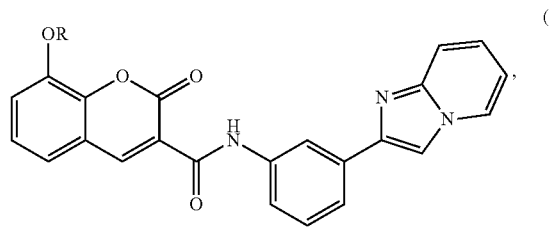

(I)

wherein R is H or Me;
(b) the compound PAC-1:

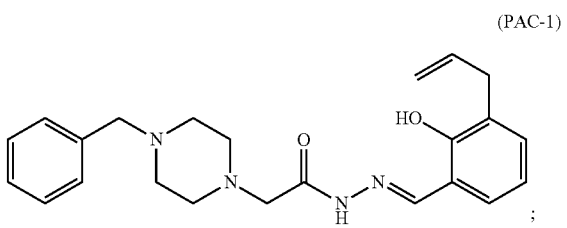 [SMILES: C=CCc1cccc(/C=N/NC(=O)CN2CCN(Cc3ccccc3)CC2)c1O]

(PAC-1)

and (c) a pharmaceutically acceptable diluent, excipient, or carrier. In one embodiment, R of Formula (I) is H. In another embodiment, R of Formula (I) is Me. The carrier can include water, and optionally a buffer, a cyclodextrin, or a combination thereof. In one specific embodiment, cyclodextrin is 2-hydroxypropyl-β-cyclodextrin.

The invention also provides a method of inhibiting the growth or proliferation of cancer cells comprising contacting cancer cells with an effective amount of a compound or composition described herein, thereby inhibiting the growth or proliferation of the cancer cells. The cancer cells can be cells of anal cancer, bladder cancer, breast cancer, cervical cancer, colorectal cancer, gastric cancer, head and neck cancer, leukemia, lung cancer Hodgkin's lymphoma, Non-Hodgkin's lymphoma, malignant lymphoma, neuroblastomas, ophthalmic cancer, osteogenic carcinomas, ovarian cancer, prostate cancer, renal cancer melanoma, soft tissue sarcomas, thyroid cancer, or Wilms' tumor. In some embodiments, the cancer cells are breast cancer cells, leukemia cells, or lymphoma cells.

The invention further provides a method of activating procaspase-3 to caspase-3 comprising contacting the procaspase-3 with a compound or composition described herein. The contacting for this method, or other methods described herein, can be in vitro, or the contacting can be in vivo.

The invention also provides a method of potentiating the activity of a compound of Formula (I):

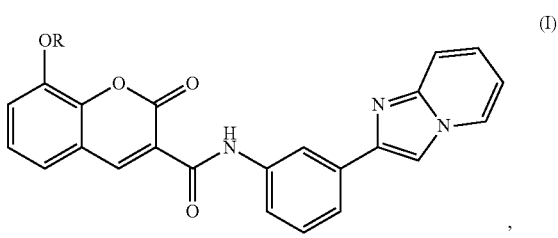

(I)

wherein R is H or Me;
comprising contacting a cancer cell with a combination of the compound of Formula I and an effective activating amount of PAC-1:

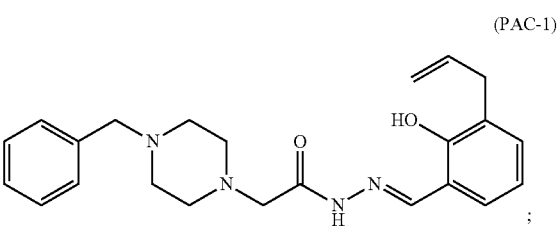 [SMILES: C=CCc1cccc(/C=N/NC(=O)CN2CCN(Cc3ccccc3)CC2)c1O]

(PAC-1)

wherein the PAC-1 potentiates the activity of the compound of Formula (I) toward the cancer cell.

The invention additionally provides a method of inducing apoptosis in a cancer cell comprising contacting the cancer cell with an effective amount of a compound of Formula (I):

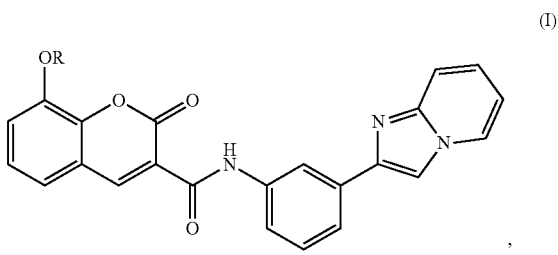

(I)

wherein R is H or Me;
and an effective amount of the compound PAC-1:

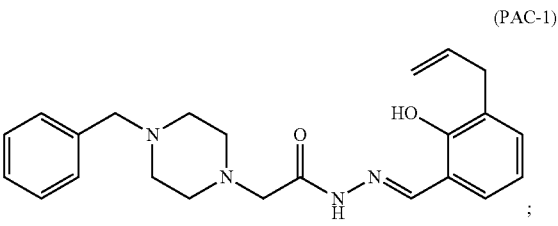 [SMILES: C=CCc1cccc(/C=N/NC(=O)CN2CCN(Cc3ccccc3)CC2)c1O]

(PAC-1)

wherein apoptosis is thereby induced in the cancer cell. The cancer cell can be contacted with the compound of Formula (I) and the PAC-1 concurrently. Alternatively, the cancer cell can be contacted with the compound of Formula (I) prior to contacting the cancer cell with PAC-1, or the cancer cell can be contacted with PAC-1 prior to contacting the cancer cell with the compound of Formula (I).

The invention further provides a method of treating a cancer in a patient in need thereof comprising administering to a patient, concurrently or sequentially, a therapeutically effective amount of a compound of Formula (I):

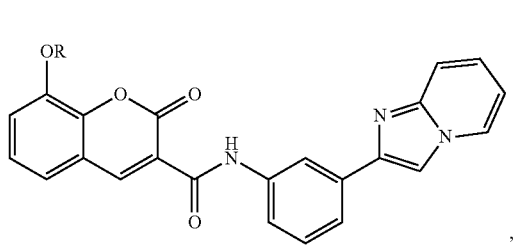

(I)

wherein R is H or Me;
and an effective amount of the compound PAC-1:

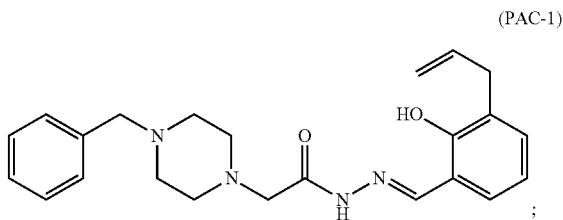 [SMILES: C=CCc1cccc(/C=N/NC(=O)CN2CCN(Cc3ccccc3)CC2)c1O]

(PAC-1)

wherein the cancer is breast cancer, leukemia, or lymphoma. The compound of Formula (I) and the compound PAC-1 can be administered concurrently. In another embodiment, the compound of Formula (I) and the compound PAC-1 can be administered sequentially. In some embodiments, the compound of Formula (I) is administered before the compound PAC-1. In other embodiments, the compound of Formula (I) is administered after the compound PAC-1.

The invention thus provides for the use of the compositions described herein for use in medical therapy. The medical therapy can be treating cancer, for example, breast cancer, lung cancer, pancreatic cancer, prostate cancer, colon cancer, and other cancers recited herein. The invention also provides for the use of a composition as described herein for the manufacture of a medicament to treat a disease in a mammal, for example, cancer in a human. The invention thus provides for the use of the compounds described herein for the manufacture of medicaments useful for the treatment of cancer in a mammal, such as a human. The medicament can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

FIG. 7. PAC-1/1541B combinations induce rapid death of cancer cells in culture. Cancer cell lines were treated with the indicated concentrations of PAC-1 and 1541B and apoptotic death was assessed. Data shown are for U-937, A549, and BT-549, as indicated. The dotted lines represent an additive effect of PAC-1 and 1541B for each drug combination.

FIG. 8. Activation of procaspase-3 to caspase-3 was observed in A) HL-60 (human promyelocytic leukemia), B) Hs578T (human breast cancer), and C) U-87 (human glioblastoma), and D) EL4 (murine lymphoma) cells lines upon treatment with the PAC-1/1541B combinations, whereas low/no procaspase-3 activation was observed with 1541B or PAC-1 alone. The dotted lines represent an additive effect of PAC-1 and 1541B for each drug combination.

FIG. 9. Additional data and data at various concentrations obtained by the methods used for FIGS. 7 and 8. 11A) Jurkat cells; 11B) EL-4 cells; 11C) HL-60 cells; 11D) A-549 cells; and 11E) BT-549 cells. The dotted lines represent an additive effect of PAC-1 and 1541B for each drug combination. The legends correspond to the bars of the bar graph where the top legend entry corresponds to the left-most bar, and the remaining legend entries correspond to the remaining bars, top to bottom corresponding to left to right, respectively.

DETAILED DESCRIPTION

Figure 1:
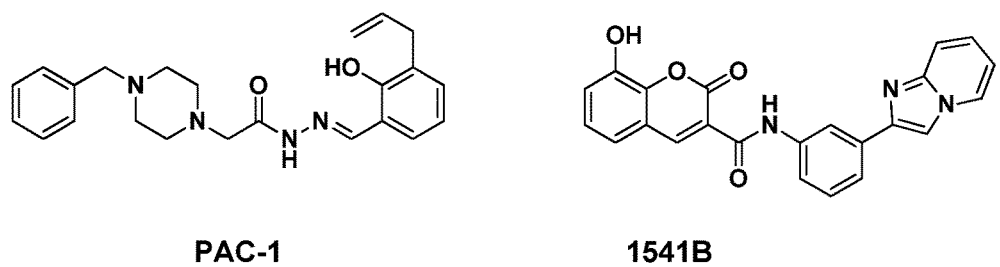
FIG. 1. Structures of PAC-1 and 1541B.

As a further introduction, compounds capable of activating an enzyme that is often overexpressed or otherwise present at increased levels in its inactive form in cancer cells have been discovered. The compounds can induce programmed cell death (apoptosis) in cancer cells, including those that have upregulated or increase levels of procaspase-3. Many cancers resist standard chemotherapy. The combination therapy described herein can take advantage of a biological target that may be upregulated in cancer cells and thus can prove effective even in cells with defects in their apoptotic machinery, while providing efficacy under conditions where one of the combination alone would be less effective or ineffective. These compounds can also be successful in targeted cancer therapy, where there can be advantages of selectivity in the killing of cancer cells with comparably reduced adverse reactions to non-cancerous cells having lower levels of procaspase-3. These adverse reactions can include toxicity, particularly neurotoxicity.

The combination of compounds, compositions and methods described herein can act via modulation of apoptosis or programmed cell death to be effective in the treatment of cancer cells. In one embodiment, the modulation of apoptosis is by induction of apoptosis. In various embodiments, the administration of compounds can be concurrent, or alternatively, sequential.

The invention thus provides methods for potentiation, not based on compounds acting on two targets within a single pathway, but rather through two compounds acting differentially on the same protein. During apoptosis, the zymogen procaspase-3 is activated via proteolysis to caspase-3, and this active caspase-3 then cleaves scores of cellular substrates, executing the apoptotic program. Because procaspase-3 protein levels are elevated in various tumor histologies, drug-mediated direct activation of procaspase-3 can be highly effective as a selective anticancer strategy.

To date, two classes of compounds have been disclosed that enhance the activity and automaturation of procaspase-3 in vitro, and induce apoptosis in cancer cells in culture. Procaspase-activating compound-1 (PAC-1, FIG. 1) enhances the activity of procaspase-3 via the chelation of inhibitory zinc ions, induces apoptosis in cancer cells in culture, and has efficacy in multiple murine tumor models. More recently, the compounds 1541 and 1541B (FIG. 1) were discovered to promote the automaturation of procaspase-3 to caspase-3 in vitro and to induce apoptotic death of cancer cells in culture (Wolan et al., Science 326, 853-858 (2009)). The 1541/1541B compounds appear to activate procaspsae-3 via a binding-induced shift in the on-off state equilibrium, or through formation of nanofibrils, with the precise mechanism likely dependent on compound concentration and complexity of the system in which procaspase-3 is evaluated. PAC-1 and 1541/1541B exert their respective activating effect on procaspase-3 by distinct biochemical mechanisms, indicating the potential for synergistic effects in vitro, in cell culture, and in vivo.

Therapeutic Agents and Activity

PAC-1 (2-(4-benzylpiperazin-1-yl)-N-[(2-hydroxy-3-prop-2-enyl-phenyl)methylideneamino]acetamide), illustrated in FIG. 1, selectively induces apoptosis in cancerous cells. Methods of preparing PAC-1 are described in U.S. Patent Publication No. 2012/0040995 (Hergenrother et al.).

The drugs known as compounds 1541 and 1541B (Scheme 1 below) may act to induce procaspase-3 automaturation by inducing an 'on-state' conformation of procaspase-3 that enhances the latent activity of the proenzyme, or by induction of a procaspase-3 conformation that make it a better substrate for the automaturation. The compounds may also promote procaspase-3 cleavage through increasing local concentration through binding on 1541B nanofibrils.

Scheme 1.

Formula (I)

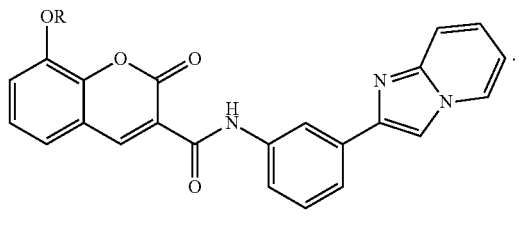

1541: R = Me
1541B: R = H

Figure 2:
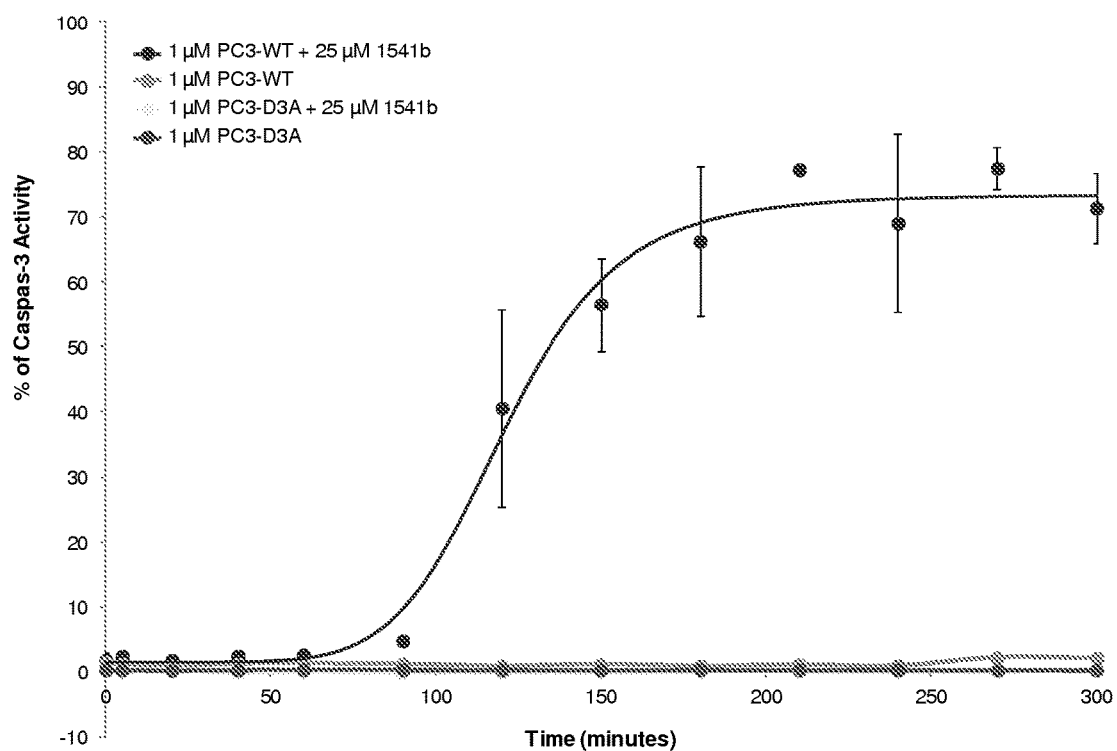
FIG. 2. Wild-type procaspase-3 (1 μM) or the $D_3A$ mutant (1 μM) were incubated with compound 1541B (25 μM) at 37° C., and caspase-3 activity was monitored by taking aliquots at the indicated time points and evaluating them with the Ac-DEVD-AFC substrate. Caspase-3 (at 1 μM) was used to set the 100% caspase-3 activity. Lines in the figure correspond to the figure legend, top to bottom, respectively (1 μM PC3-WT+25 μM 1541B on top).

As a prelude to synergy studies, studies were undertaken to clarify how 1541B acts to induce procaspase-3 automaturation. To further clarify the mechanism, a mutant of procaspase-3 was used where the three proteolytic cleavage sites (D9, D28, D175) were mutated to alanines (the D9A/D28A/D175A or "$D_3A$" mutant protein). This $D_3A$ "uncleavable" version is fully resistant to autoprocessing and to processing by mature caspases. Because it is constrained to the zymogen form, it can act only as an enzyme, not as a caspase substrate. The $D_3A$ mutant has been used previously to show that procaspase-3 itself possesses latent enzymatic activity, albeit 200-fold less than caspase-3 (Bose et al., Biochemistry 42, 12298-12310 (2003)). Upon incubation with 1541B, wild-type procaspase-3 was activated as expected, but 1541B had no effect on D₃A (FIG. 2), indicating that 1541B does not enhance the intrinsic enzymatic activity of procaspase-3.

Figure 3:
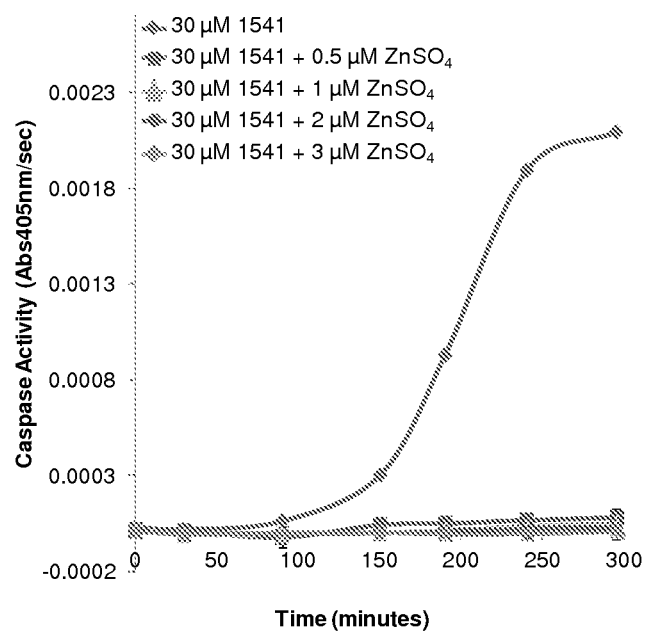
FIG. 3. Wild-type procaspase-3 (1 μM) was incubated with 1541B (25 μM) in the presence of a range of $ZnSO_4$ concentrations, and caspase-3 activity was monitored with the Ac-DEVD-pNA substrate. Lines in the figure correspond to the figure legend, top to bottom, respectively.
Figure 4:
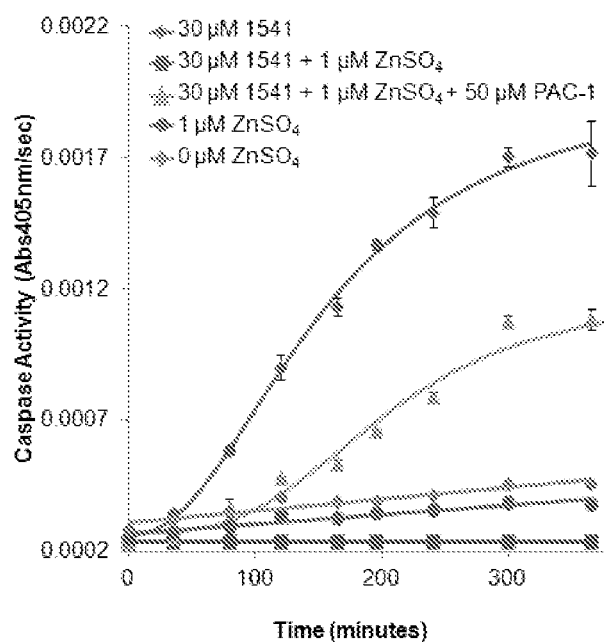
FIG. 4. Wild-type procaspase-3 (1 μM) was incubated with $ZnSO_4$ (1 μM) and 1541B (25 μM), or 1541B (30 μM) and PAC-1 (50 μM), and caspase-3 activity was monitored with the Ac-DEVD-pNA substrate. Lines in the figure correspond to the figure legend, top to bottom, respectively. PAC-1 thus potentiates the 1541B activity.

The activating effect of compound 1541B on procaspase-3 in vitro had previously only been evaluated under zinc free conditions, while PAC-1 enhances the catalytic activity of both procaspase-3 and D3A via chelation of inhibitory zinc. As zinc co-localizes with procaspase-3 and inhibits its cleavage to the active form in the cell, it was of interest to determine if 1541B could activate procaspase-3 in the presence of low concentrations of zinc. As shown in FIG. 3, the inclusion of zinc completely prevents the ability of 1541B to activate procaspase-3 in vitro. However, the addition of PAC-1 allows 1541B to once again activate procaspase-3 (FIG. 4), showing the PAC-1-mediated potentiation of 1541B.

Figure 5A:
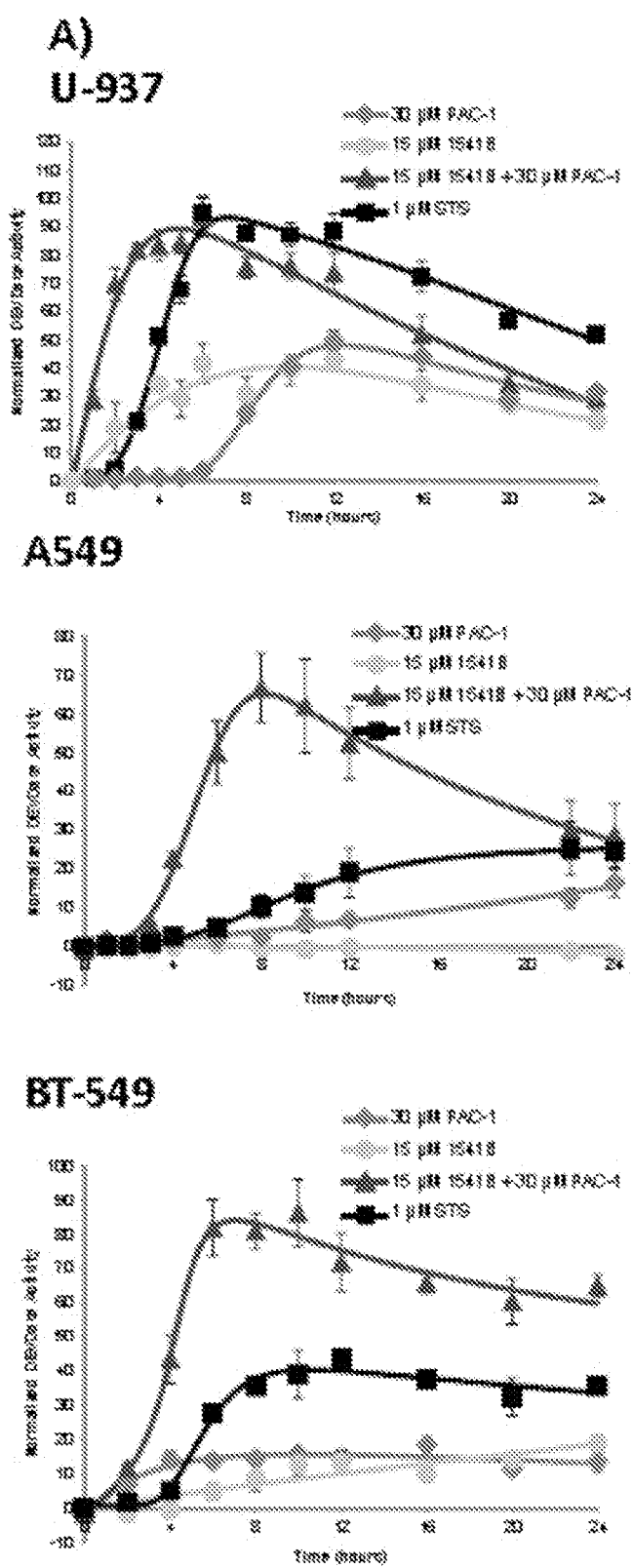
FIG. 5. PAC-1/1541B combinations induce rapid and dramatic procaspase-3 maturation and activation. A: The caspase-3/-7-like activity of cancer cell lysates after treatment with the PAC-1/1541B combinations. STS=staurosporine. B: Western blot of various cancer cell lines (using Cell Signaling caspase-3 antibody) after treatment with combinations of PAC-1 and 1541B.

To examine if PAC-1 similarly potentiated 1541B-mediated activation of procaspase-3 in cancer cells in culture, a panel of cancer cell lines were treated with combinations of PAC-1 and 1541B and the caspase-3/-7 activity of the cell lysates was monitored with the fluorogenic caspase substrate Ac-DEVD-AFC. As shown in FIG. 5A, co-treatment resulted in markedly more rapid and dramatic increases in DEVDase cleavage than either PAC-1 or 1541B alone; the combination induces caspase activity that rivals or surpasses that induced by staurosporine (STS, 1 μM). The DEVDase activity of U-937 (human lymphoma), A-549 (human lung cancer), and BT-549 (human breast cancer) lysates are shown in FIG. 5, and analogous data with HL-60 (human leukemia), Jurkat (human leukemia), Hs578T (human breast cancer), and EL4 (canine lymphoma) cell lines was obtained.

Figure 5B:
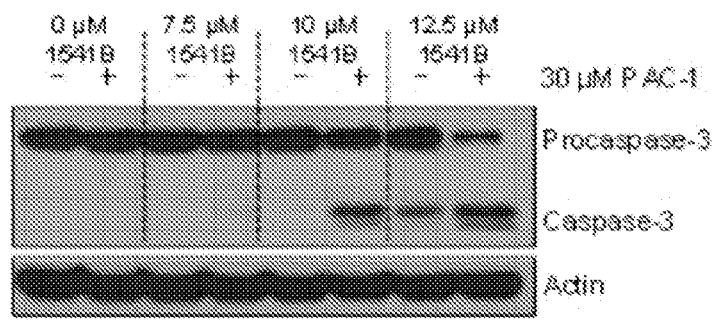
Figure 5B:
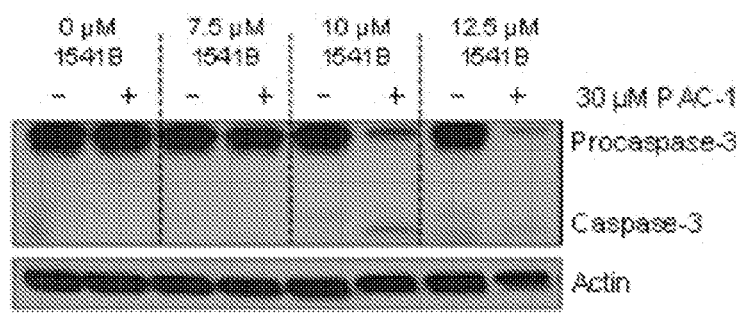
Figure 5B:
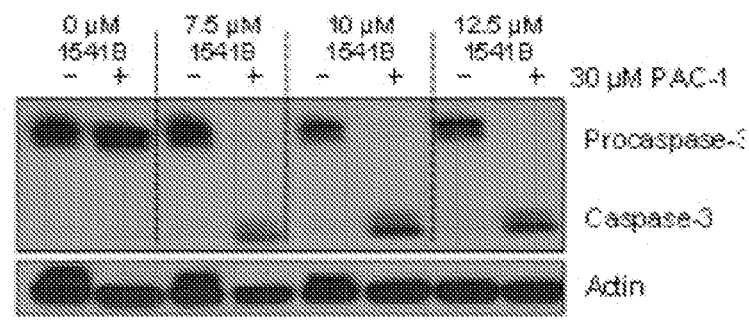
Figure 6D:
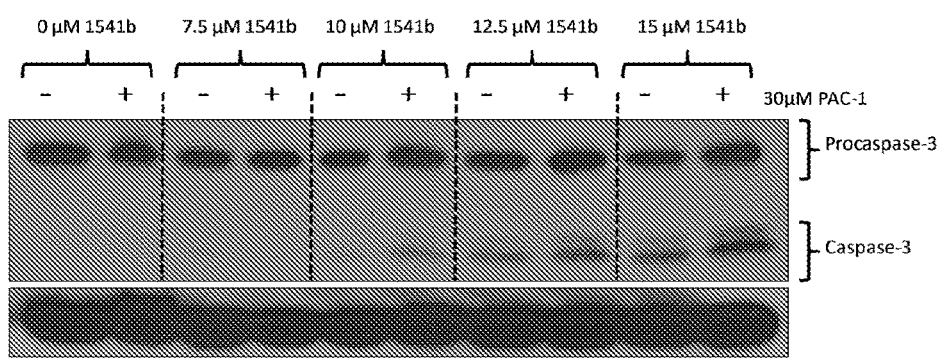
FIG. 6. Data analogous to FIG. 5B with A: HL-60 (human leukemia), B: EL4 (murine lymphoma), C: Hs578T (human breast cancer), and D: Jurkat (human leukemia) cell lines.

To determine if the elevation of DEVDase activity was the result of enhanced cleavage of procaspase-3 to caspase-3 facilitated by compound co-treatment, cells treated with PAC-1 and 1541B combinations were assessed by Western blot. As shown in FIG. 5B, dramatic activation of procaspase-3 to caspase-3 was observed in U-937, A549, and BT-549 cell lines upon treatment with the PAC-1/1541B combinations, whereas low/no procaspase-3 activation was observed with 1541B or PAC-1 alone at the times and concentrations evaluated. Analogous results in HL-60, EL4, Hs578T, and Jurkat cells are shown in FIGS. 6A-D.

Figure 7:
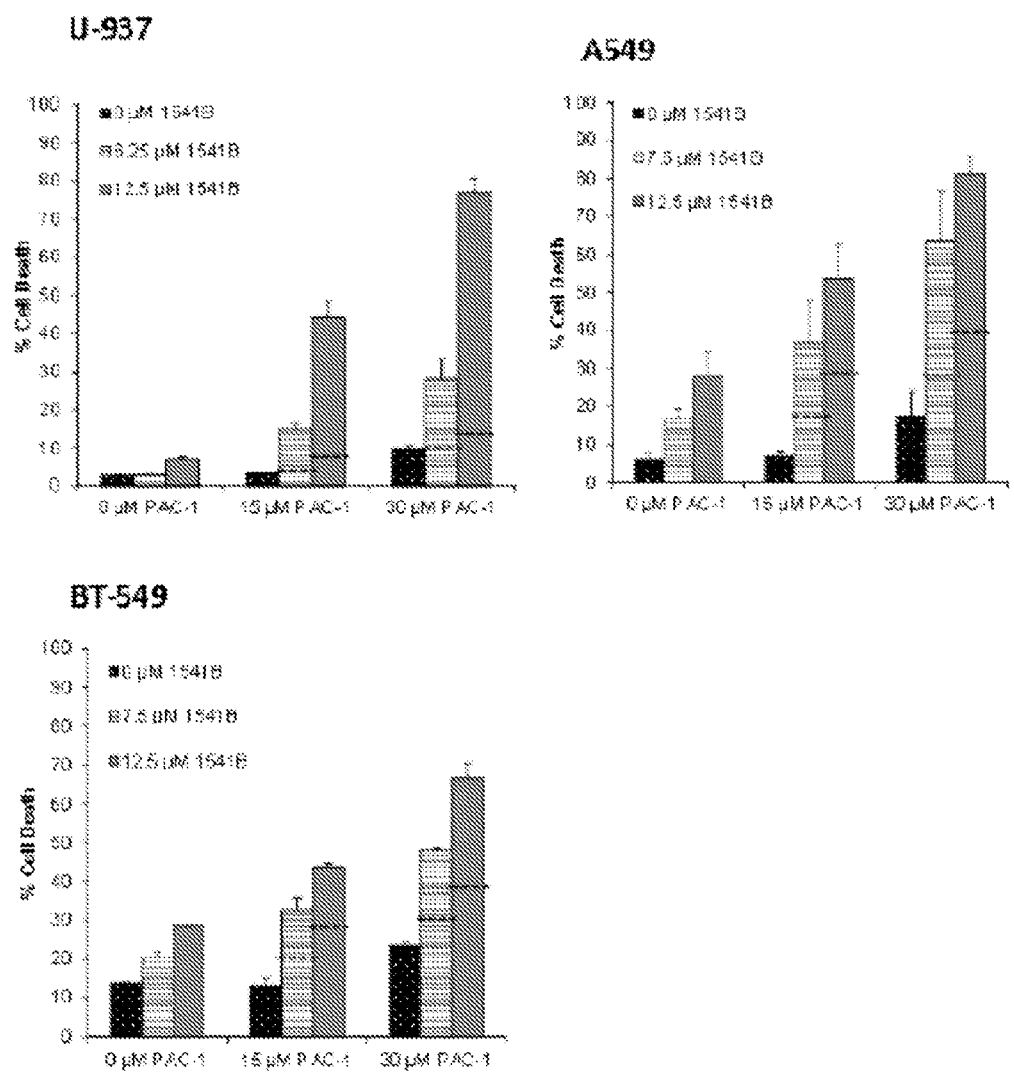
FIGS. 7-9. PAC-1 significantly potentiates the pro-apoptotic activity of 1541B in a variety of different cell lines.
Figure 8:
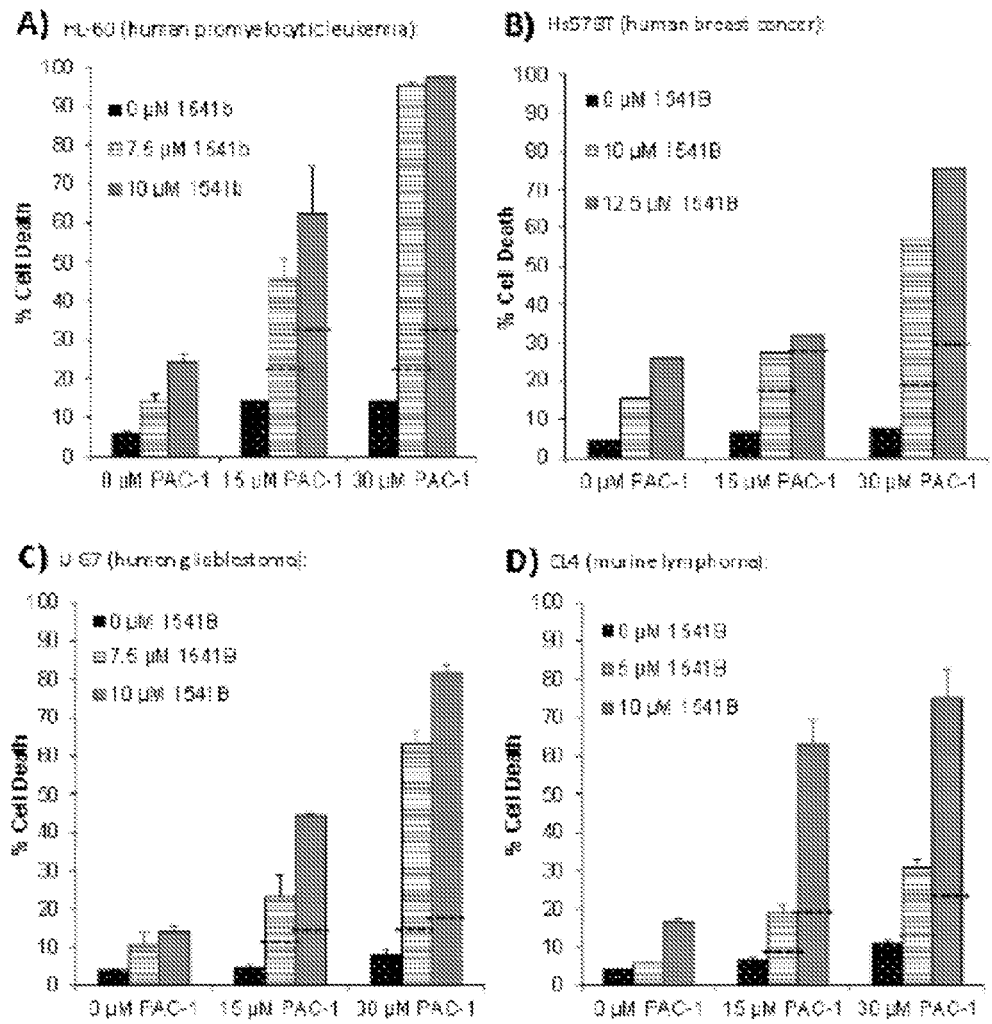
Figure 9A:
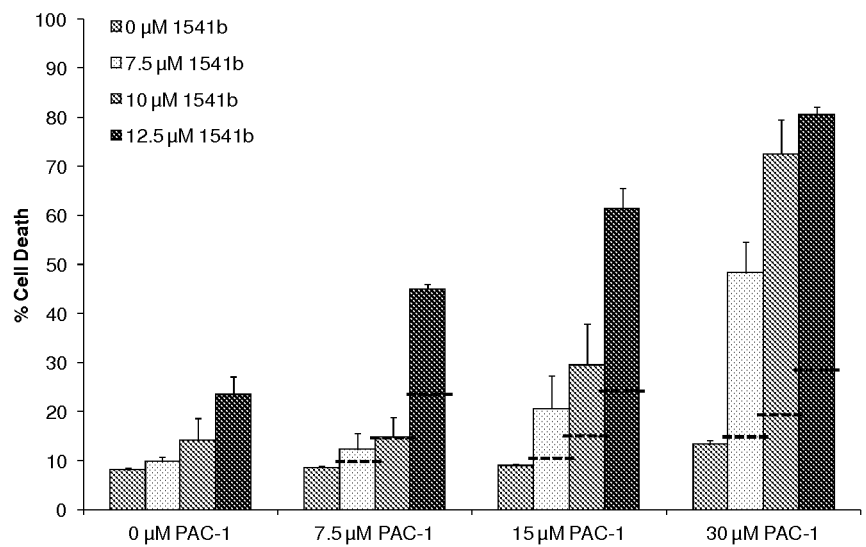
Figure 9B:
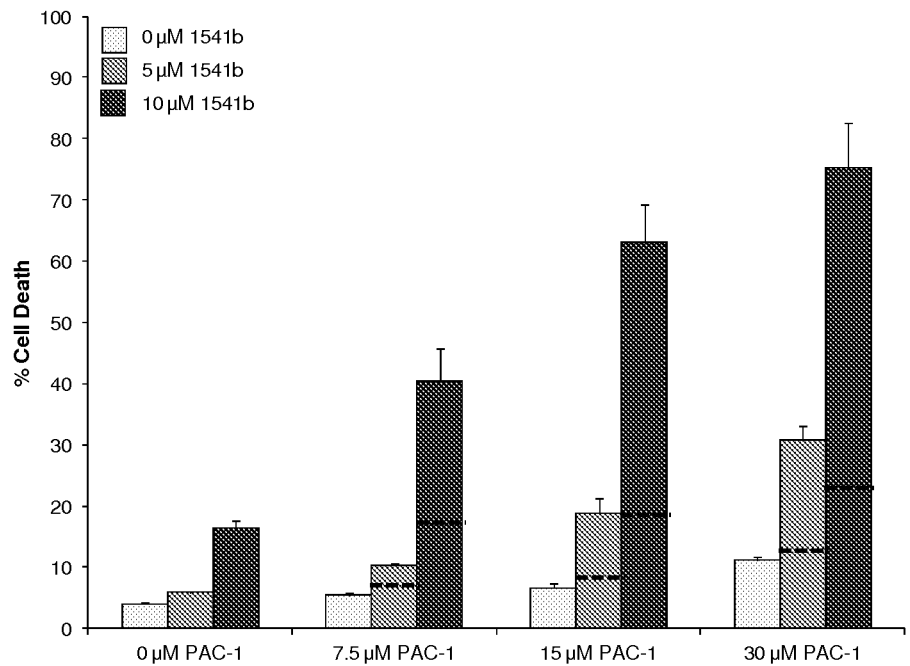
Figure 9C:
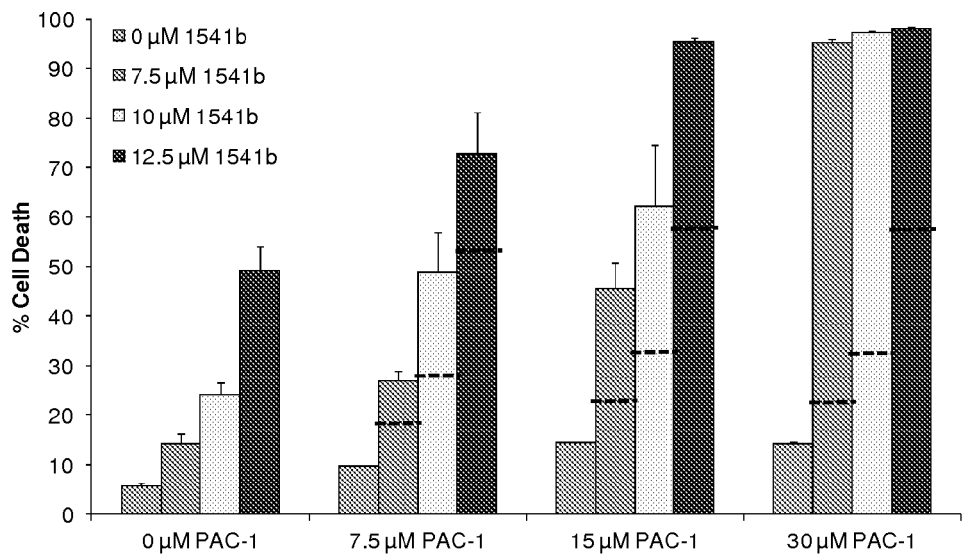
Figure 9D:
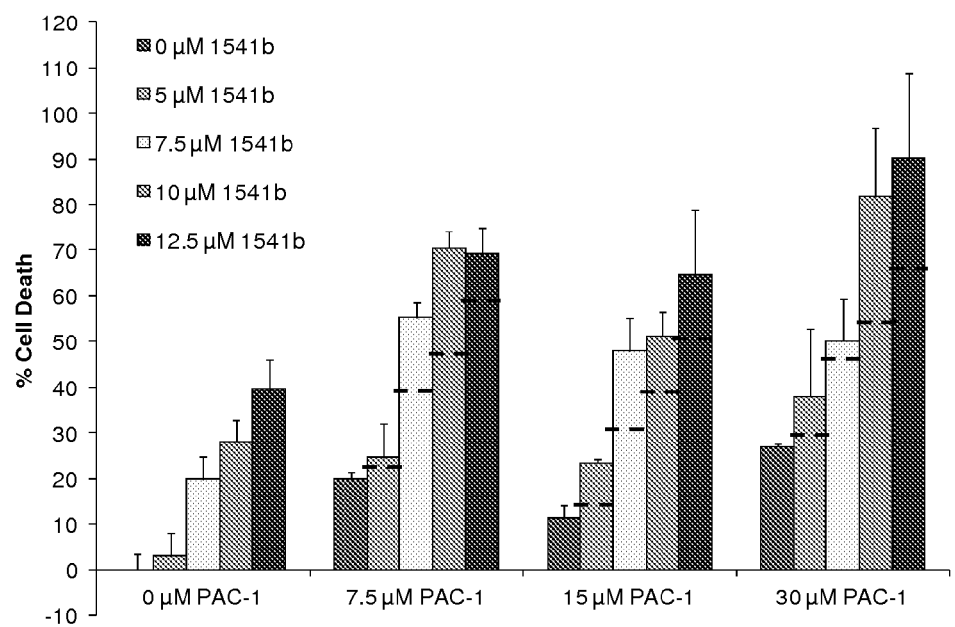
Figure 9E:
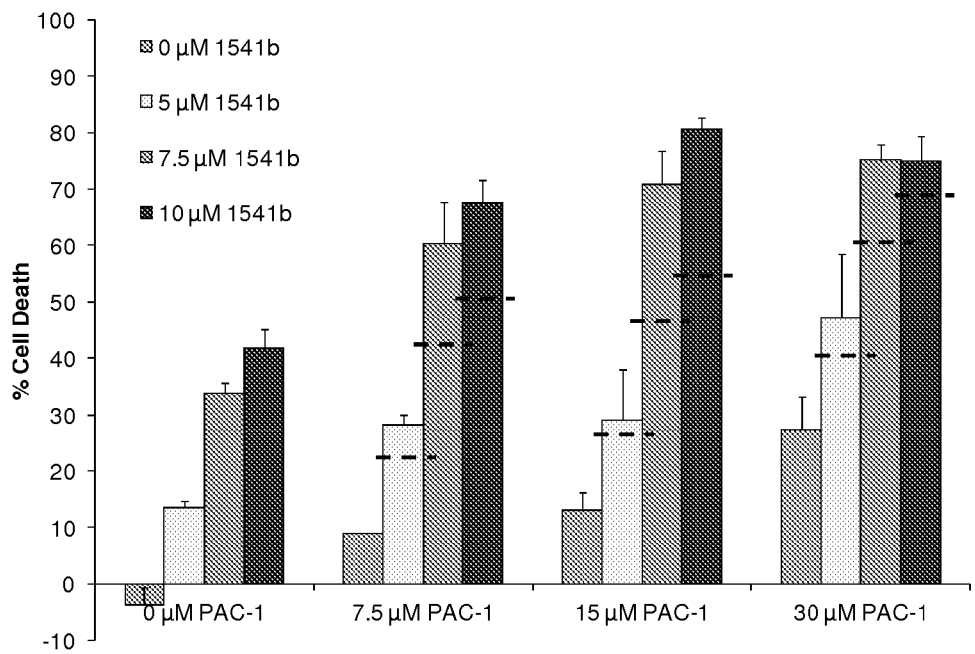

As cleavage of procaspase-3 to caspase-3 is one of the major events in apoptosis, the combination of PAC-1 and 1541B was evaluated for the capacity to induce apoptotic death in a variety of cancer cell lines in culture. These evaluations were performed at short incubation times, reflective of the timing of caspase activation observed in FIG. 5, where neither compound exerted a significant effect as a single-entity agent. PAC-1 significantly potentiates the proapoptotic activity of 1541B, which was assessed using flow cytometry with Annexin V/propidium iodide staining (suspension lines U-937, HL-60, and Jurkat), or cell death was assessed by sulforhodamine B staining in adherent lines (A549 and BT549). Cell death data for U-937, A549, and BT-549 cells is shown in FIG. 7. Cell death data for HL-60, Hs578T, U-87, and EL4 is shown in FIG. 8A-D. Cell death data for Jurkat, EL4, HL-60, A549, and BT549 cells is shown in FIG. 9A-E. The dotted lines in each graph represent the additive effect of PAC-1 and 1541B for the drug combination.

Figure 10:
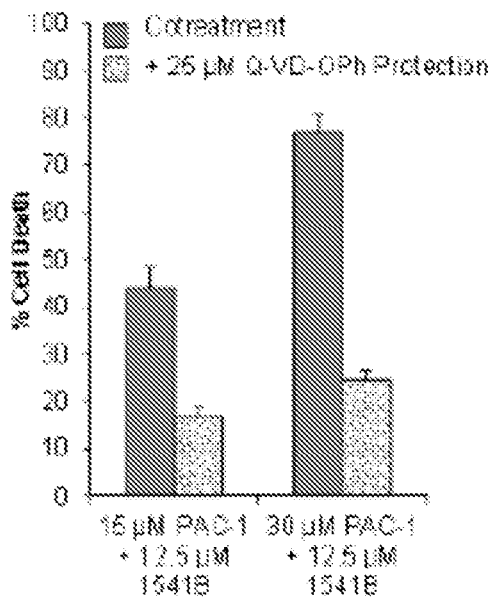
FIG. 10. The pan-caspase inhibitor Q-VD-OPh (25 μM) protects against PAC-1/1541B-mediated cell death in MCF-7 cells.
Figure 11:
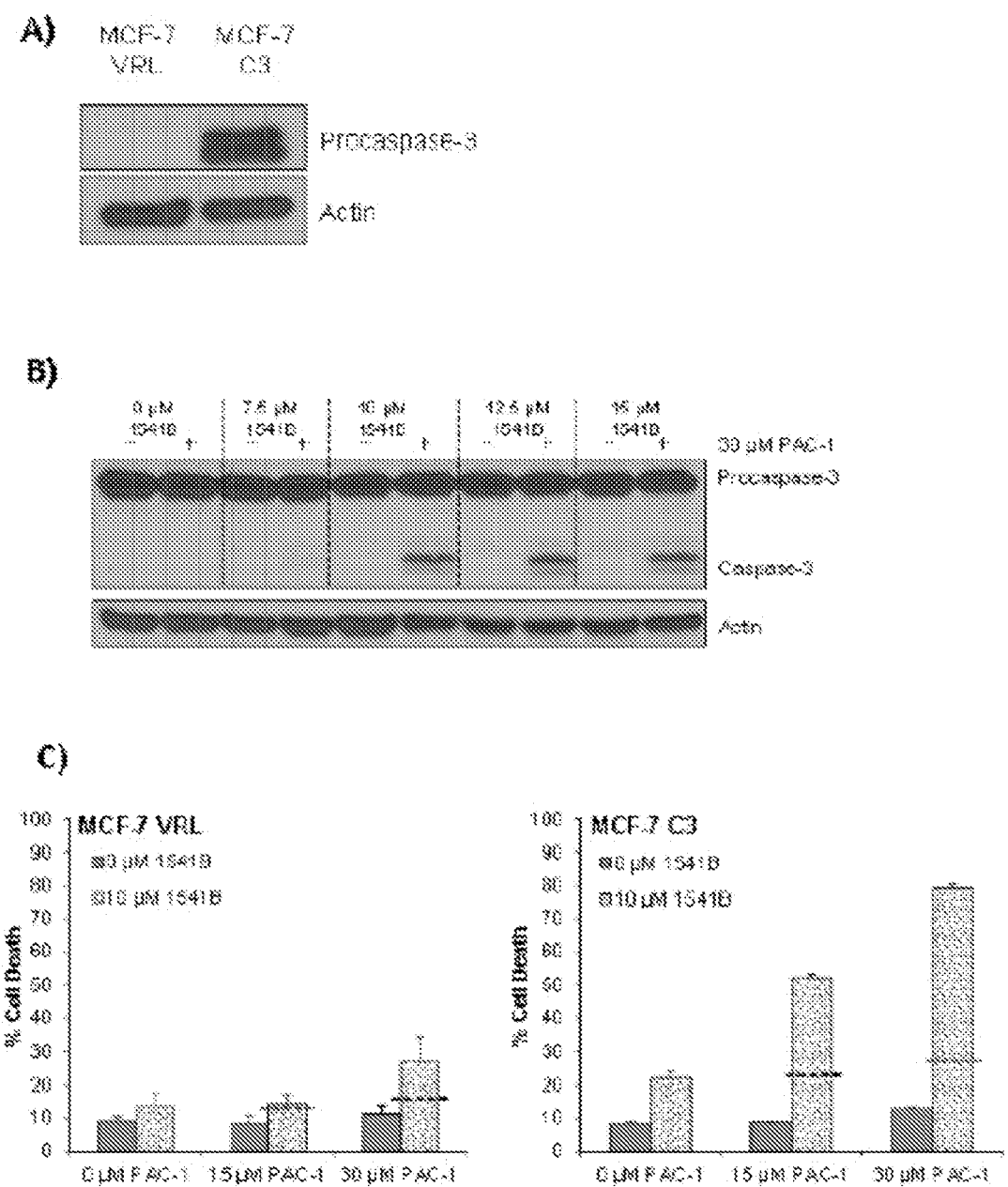
FIG. 11. The combination of PAC-1/1541B had minimal effect on MCF-7 cells (MCF-7 VRL), but had a dramatic pro-apoptotic effect on MCF-7 cells that express procaspase-3 via a plasmid (MCF-7 C3). A) Western blot of MCF-7 VRL vs. MCF-7 C3. B) Western blot using various concentrations of 1541B, showing caspase-3 activation. C) MCF-7 cell death data; C3 knock-in pair.

The proapoptotic effect of the PAC-1/1541B combination was blocked with the pan-caspase inhibitor Q-VD-OPh, consistent with the involvement of caspases in the mode of cell death (FIG. 10). To further investigate the connection between activation of procaspase-3 and the cell death induced by the drug combination, MCF-7 cells were used, a cell line that does not express procaspase-3. The combination of PAC-1/1541B had minimal effect on MCF-7 cells (MCF-7 VRL), but had a dramatic proapoptotic effect on MCF-7 cells that express procaspase-3 via a plasmid (MCF-7 C3). See FIG. 11A-C.

Figure 12:
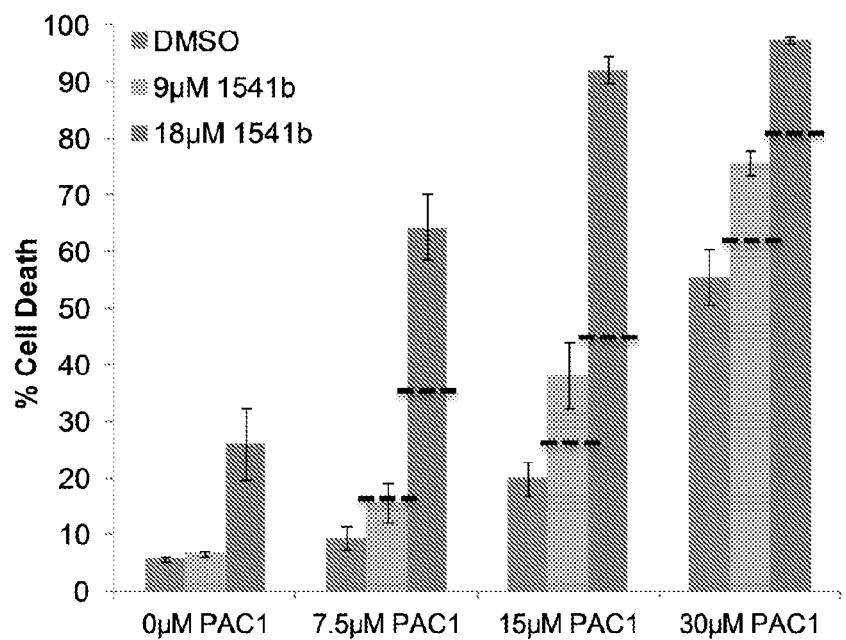
FIG. 12. Synergistic effects of PAC-1 (A) with 1541B in U-937 cells. Synergistic effect of PAC-1 with 1541b in EL4 cells (B). Dashed lines represent the expected level of purely additive effects. The legends correspond to the bars of the bar graph where the top legend entry corresponds to the left-most bar, and the remaining legend entries correspond to the remaining bars, top to bottom corresponding to left to right, respectively.
Figure 12:
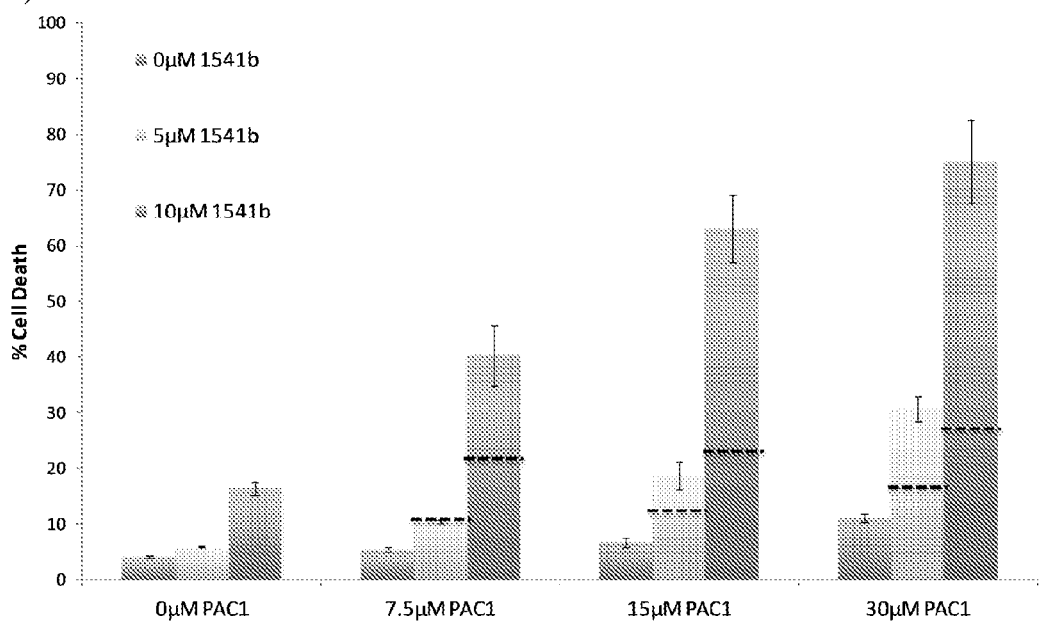
Figure 13:
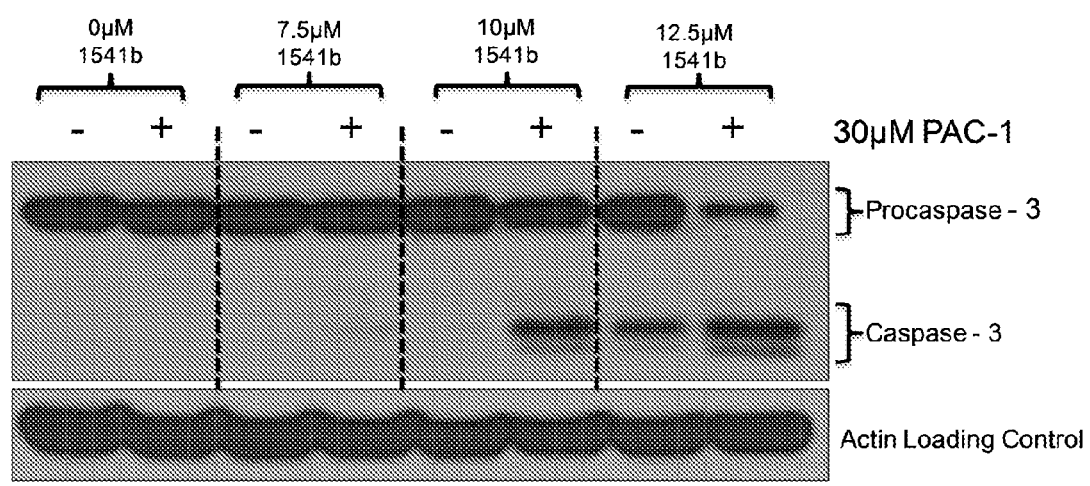
FIG. 13. Western blot procaspase3 activation analysis of U-937 cells treated with increasing concentrations of 1541B and either with or without PAC-1.
Figure 14:
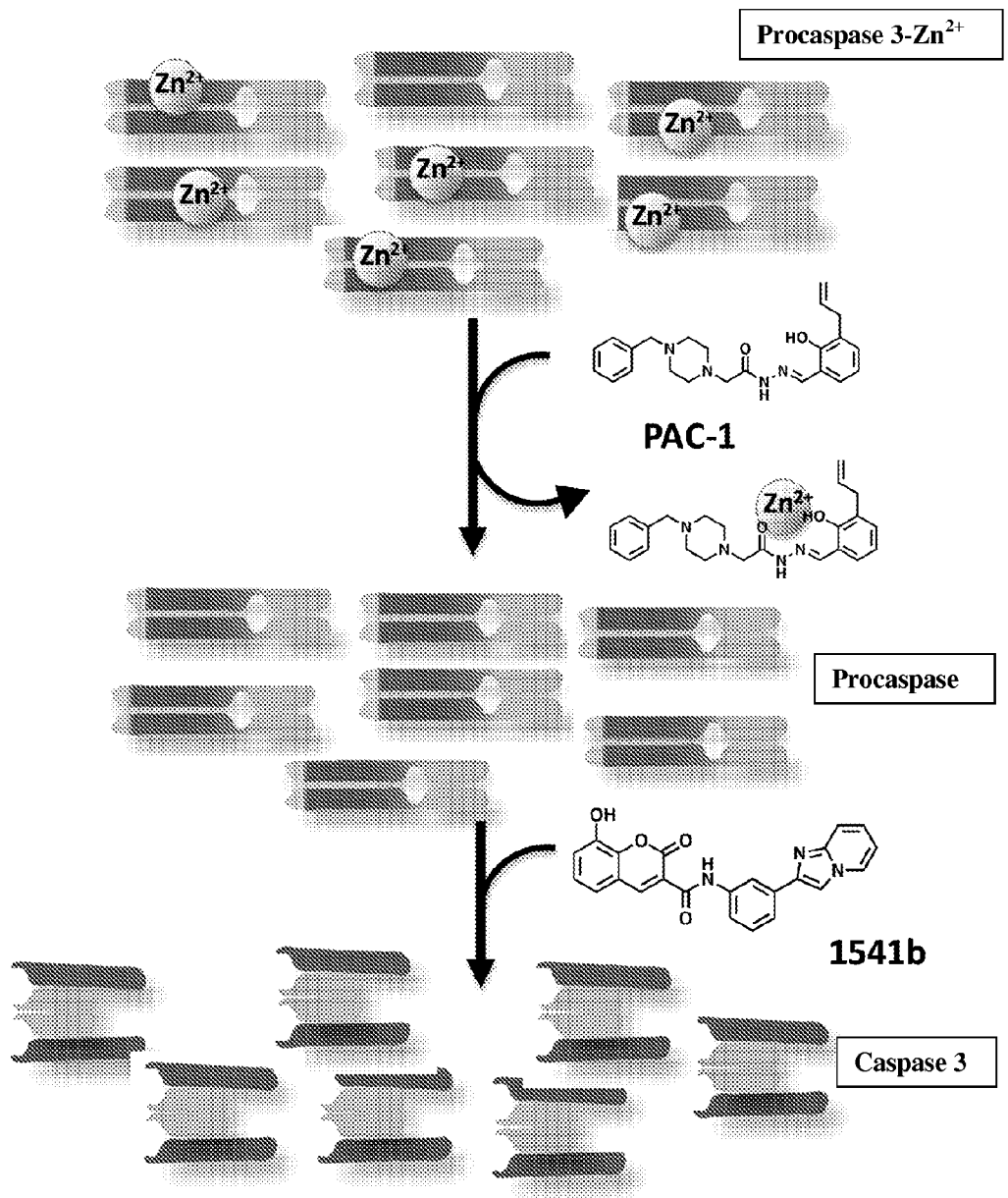
FIG. 14. Schematic of a mechanism showing the combined activation of procaspase 3 by PAC-1 and 1541B.

As discussed above, compound 1541B does not activate procaspase 3 via the same zinc chelation mechanism that is the mode of action for PAC-1 and related compound. Rather 1541 operates by an allosteric binding and activation mechanism. The combination of PAC-1 and 1541B was also found to be a synergistic combination for the treatment of lymphoma and leukemia, as demonstrated against U-937 and EL4 tumor cell lines. PAC-1 was demonstrated to work synergistically with 1541B in two lymphoma/leukemia cell lines where the percent cell death upon treatment with the combination of compounds is significantly greater that what would be expected based on purely additive effects (FIG. 12). Western Blot analysis demonstrated that greater levels of procaspase 3 activation are achieved (FIG. 13) with the combination and is consistent with the mechanism shown in FIG. 14.

To explore the therapeutic utility of this dual procaspase-3 activation strategy, the combination of PAC-1 and 1541B were examined in a murine tumor model. The EL4 syngeneic model was chosen, as PAC-1 and 1541B synergize to induce dramatic cell death versus this cell line, and it is a challenging treatment model due to rapid growth of tumors.

C57/BL6 mice implanted with EL4 (murine lymphoma) cells were treated with PAC-1 alone (125 mg/kg), 1541B alone (17.5 mg/kg), and PAC-1+1541B (125 mg/kg and 17.5 mg/kg, respectively) once-a-day for three days. The dosages selected were based on maximal tolerated dose (MTD) studies (see Tables 1 and 2 for MTD studies).

TABLE 1

1541B MTD Study.

| 1541B Dosage (mg/kg in HPβCD) | Number of Consecutive Daily Treatments | Result |
|---|---|---|
| 5 | 5 | 3/3 mice asymptomatic |
| 10 | 5 | 3/3 mice asymptomatic |
| 15 | 5 | 3/3 mice asymptomatic |
| 20 | 5 | 3/3 mice survived |
| 25 | 3 | 2/3 mice survived treatment with 20% weight loss |
| 50 | 1 | 3/3 mice were symptomatic for 3 days prior to full recovery |

TABLE 2

Combination MTD Study.

| Fraction of MTD | PAC-1 Dosage (mg/kg) | 1541B Dosage (mg/kg) | Result |
|---|---|---|---|
| 1/10 | 20 | 2 | 3/3 mice asymptomatic |
| 1/6 | 33.3 | 3.3 | 3/3 mice asymptomatic |
| 1/3 | 66.7 | 6.67 | 3/3 mice asymptomatic |
| 1/2 | 100 | 10 | 3/3 mice asymptomatic |
| 3/4 | 150 | 15 | 3/3 mice survived treatment but displayed minor toxicity out to 24 hours |
| 'Sub Toxic Effect Level' | 125 | 17.5 | 3/3 mice asymptomatic |

Figure 15:
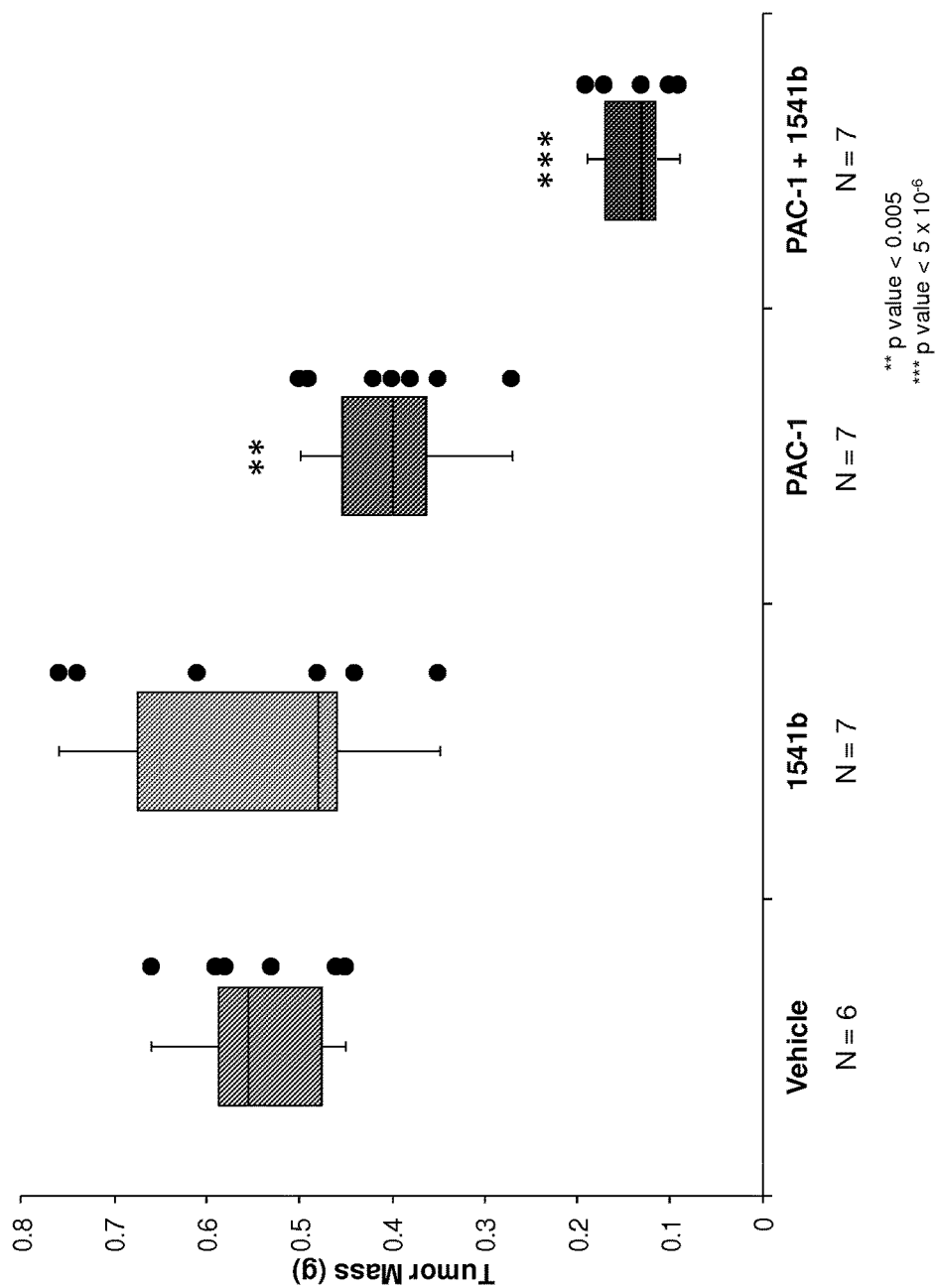
FIG. 15. The combination of PAC-1 and 1541B has an antitumor effect in vivo. EL4 cells (10 million cells per mouse) were injected subcutaneously into mice, the animals were split into four groups and treated with vehicle (2-hydroxypropyl-β-cyclodextrin, HPβCD), 1541B (at 17.5 mg/kg in HPβCD), PAC-1 (125 mg/kg in HPβCD), or 1541B+PAC-1 (17.5 and 125 mg/kg, respectively, in HPβCD). After eight days the mice were sacrificed and the tumors excised and weighed. Error bars equal standard error, and p-values indicated are relative to vehicle control.

After 8 days when the tumors in the vehicle-treated mice had achieved maximal size (~1500 mm³), all mice were sacrificed and tumors were excised and weighed. As shown in FIG. 15, 1541B treatment had no effect, and PAC-1 treatment had only minimal effect on tumor growth in this model. However, the combination of PAC-1 and 1541B dramatically retarded tumor growth.

While there is clear benefit to anticancer strategies utilizing combinations of drugs that act on different targets, the work described herein demonstrates that dramatic synergy can be observed with compounds that act through disparate mechanisms on the same biological target. This multi-targeting approach may have particular advantages when activation of an enzyme is sought. As shown in vitro, 1541B is unable to activate procaspase-3 in the presence of zinc, but the addition of PAC-1 allows 1541B to once again exert its effect. PAC-1 chelates the labile inhibitory zinc from pro-caspase-3, thus priming this zymogen for robust and efficient activation by 1541B.

Similarly, in cell cultures neither compound has a significant cell death effect at 6-12 hours, but dramatic enhancement of cell death (greater than the additive effect) is observed with the PAC-1/1541B combination. This cell death is tied to the ability of the PAC-1/1541B to induce a rapid conversion of procaspase-3 to caspase-3, as shown by the Western blots and the caspase-3 enzymatic activity in cell lysates.

PAC-1 is safe in mammals, and a derivative of PAC-1 was efficacious in a phase I clinical trial of pet dogs with lymphoma (Peterson et al., *Cancer Res* 70, 7232-7241 (2010)), thus the observed synergy with 1541B should have significant clinical impact. Interest in activating enzymes with small molecules is increasing rapidly. The data described herein indicate that targeting strategies using two small molecules with different activation mechanisms is a general approach for dramatic enhancement of the intended biologic effect and should have considerable clinical impact due to its efficacy.

Methods of the Invention

The invention provides methods of selectively inducing apoptosis in a cancer cell, comprising administering to a cancer cell a combination of compounds capable of modifying a procaspase-3 molecule of said cancer cell; wherein the combination of compounds is PAC-1 and a compound of Formula I, e.g., compound 1541 or compound 1541B. Also provided is a method of selectively inducing apoptosis in a cancer cell, comprising administering to a cancer cell a combination of compounds capable of modifying a procaspase-3 molecule of the cancer cell; wherein the combination of compounds is PAC-1 and a compound of Formula I, e.g., compound 1541 or compound 1541B, and wherein the cancer cell is in a patient in need of treatment.

The invention provides additional methods where the recited combination of compounds is PAC-1 and a compound of Formula I, e.g., compound 1541 or compound 1541B. Thus, the invention also provides a method of treating a cancer cell, comprising (a) identifying a potential susceptibility to treatment of a cancer cell with a procaspase activator compound; and (b) exposing the cancer cell to an effective amount of a combination of procaspase activator compounds. Also provided is a method of treating a cancer cell, comprising (a) identifying a potential susceptibility to treatment of a cancer cell with a procaspase activator compound; and (b) exposing said cancer cell to an effective amount of a combination of procaspase activator compounds; wherein the procaspase activator compounds are capable of activating at least one of procaspase-3 and procaspase-7. Also provided is a method of inducing death in a cancer cell (e.g., killing a cancer cell), comprising administering to a cancer cell a combination of compounds capable of activating a procaspase-3 molecule of the cancer cell.

The invention further provides a medicament comprising an effective amount of the combination of PAC-1 and a compound of Formula I. The medicament can be used in a method of inducing apoptosis in a cell. In some embodiments, the combination of compounds does not cross the blood-brain barrier to as extent that causes appreciable neurotoxic effects in a patient. Methods of the invention include contacting one or more cells with an effective amount of a combination of compounds described herein, in vivo or in vitro. The invention thus also provides methods of treating a cell that include contacting a cell with an effective amount of a combination of compounds described herein.

DEFINITIONS

As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* $14^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation.

The term "and/or" means any one of the items, any combination of the items, or all of the items with which this term is associated. The phrase "one or more" is readily understood by one of skill in the art, particularly when read in context of its usage. For example, one or more substituents on a phenyl ring refers to one to five, or one to four, for example if the phenyl ring is disubstituted.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percents, proximate to the recited range that are equivalent in terms of the functionality of the individual ingredient, the composition, or the embodiment.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

"Concurrently" means (1) simultaneously in time, or (2) at different times during the course of a common treatment schedule.

"Sequentially" refers to the administration of one active agent used in the method followed by administration of another active agent. After administration of one active agent, the next active agent can be administered substantially immediately after the first, or the next active agent can be administered after an effective time period after the first active agent; the effective time period is the amount of time given for realization of maximum benefit from the administration of the first active agent.

An "effective amount" refers to an amount effective to treat a disease, disorder, and/or condition, or to bring about a recited effect, such as activation or inhibition. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect. In one embodiment, an effective amount refers to an amount of the active agent described herein that are effective, either alone or in combination with a pharmaceutical carrier, upon single- or multiple-dose administration to a cell or a subject, e.g., a patient, at inhibiting the growth or proliferation, inducing the killing, or preventing the growth of hyperproliferative cells. Such growth inhibition or killing can be reflected as a prolongation of the survival of the subject, e.g., a patient beyond that expected in the absence of such treatment, or any improvement in the prognosis of the subject relative to the absence of such treatment.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate. In some embodiments, the terms "treatment", "treat" or "treated" can refer to (i) prevention of tumor growth or regrowth of the tumor (prophylaxis), (ii) a reduction or elimination of symptoms or the disease of interest (therapy) or (iii) the elimination or destruction of the tumor (cure).

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting. Additionally, the terms "induce," "inhibit," "potentiate," "elevate," "increase," "decrease," or the like denote quantitative differences between two states, and can refer to at least statistically significant differences between the two states. For example, "an amount effective to inhibit the growth of hyperproliferative cells" means that the rate of growth of the cells can be, in some embodiments, at least statistically significantly different from the untreated cells. Such terms can be applied herein to, for example, rates of proliferation.

The phrase "inhibiting the growth or proliferation" of the hyperproliferative cell, e.g. neoplastic cell, refers to the slowing, interrupting, arresting, or stopping its growth and metastasis, and does not necessarily indicate a total elimination of the neoplastic growth.

The term "cancer" generally refers to any of a group of more than 100 diseases caused by the uncontrolled growth of abnormal cells. Cancer can take the form of solid tumors and lymphomas, and non-solid cancers such as leukemia. Unlike normal cells, which reproduce until maturation and then only as necessary to replace wounded cells, cancer cells can grow and divide endlessly, crowding out nearby cells and eventually spreading to other parts of the body.

The invention provides methods for treating cancer and cancerous conditions. The term "cancerous condition" relates to any condition where cells are in an abnormal state or condition that is characterized by rapid proliferation or neoplasia. A cancerous condition may be malignant or non-malignant (e.g. precancerous condition) in nature. To farther describe a "cancerous condition", the terms "hyperproliferative", "hyperplastic", "hyperplasia", "malignant", "neoplastic" and "neoplasia" can be used. These terms can be used interchangeably and are meant to include all types of hyperproliferative growth, hyperplastic growth, cancerous growths or oncogenic processes, metastatic tissues or malignantly transformed cells, tissues or organs, irrespective of histopathologic type, stage of invasiveness, or cancerous determination (e.g. malignant and nonmalignant).

The term "neoplasia" refers to new cell growth that results in a loss of responsiveness to normal growth controls, e.g., neoplastic cell growth. A "hyperplasia" refers to cells undergoing an abnormally high rate of growth. However, these terms can be used interchangeably, as their context will reveal, referring generally to cells experiencing abnormal cell growth rates. "Neoplasias" and "hyperplasias" include tumors, which may be either benign, premalignant, carcinoma in-situ, malignant, solid or non-solid. Examples of some cancerous conditions that are within the scope of the invention include, but are not limited to, anal cancer, transitional cell bladder cancer, bone cancer, breast cancer, cervical cancer, colorectal cancer, gastric cancer, head and neck cancer, Kaposi's sarcoma, leukemia, lung cancer such as bronchogenic lung cancer, small cell lung cancer, and non-small cell lung cancer, Hodgkin's lymphoma, Non-Hodgkin's lymphoma, malignant lymphoma, neuroblastomas, osteogenic carcinomas (e.g. cancer of the bone), ophthalmic cancers (e.g. retinoblastomas and other cancers of the eye), ovarian cancer, prostate cancer, renal cancer, skin cancers such as melanoma, soft tissue sarcomas, thyroid cancer, and Wilms' tumor. Other examples of non-malignant hyperproliferative conditions (e.g. precancerous conditions) that are within the scope of the invention include, but are not limited to, adenomas, chondromas, enchondromas, fibromas, myomas, myxomas, neurinomas, osteoblastomas, osteochondromas, osteomas, papillary tumors, and the like.

The terms "leukemia" or "leukemic cancer" refer to all cancers or neoplasias of the hematopoetic and immune systems (blood and lymphatic system). These terms refer to a progressive, malignant disease of the blood-forming organs, marked by distorted proliferation and development of leukocytes and their precursors in the blood and bone marrow. Myelomas refer to other types of tumors of the blood and bone marrow cells. Lymphomas refer to tumors of the lymph tissue. Examples of leukemia include acute myelogenous leukemia (AML), acute lymphoblastic leukemia (ALL), and chronic myelogenous leukemia (CML).

Pharmaceutical Formulations

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartrate, succinate, benzoate, ascorbate, a-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. The solubility of actives can be increase by the use of cyclodextrins, such as 2-hydroxypropyl-β-cyclodextrin. For oral administration, compounds can be enclosed in hard or soft shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 1% to about 60%, or about 2% to about 25%, of the weight of a given unit dosage form. The amount of active compound in such therapeutically useful compositions is such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thiomersal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze drying techniques, which yield a powder of the active ingredient plus any additional desired ingredient present in the previously sterile-filtered solutions.

Useful dosages of the compounds described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

The combination of compounds can be conveniently administered in a unit dosage form, for example, containing 100 to 5,000 mg/m$^2$, 300 to 4,000 mg/m$^2$, 370 to 3,700 mg/m$^2$, 50 to 750 mg/m$^2$, or 750 to 4,000 mg/m$^2$ of active ingredient per unit dosage form. Each compound, individually or in combination, can also be administered at about 1 mg/kg to about 250 mg/kg, about 10 mg/kg to about 100 mg/kg, about 10 mg/kg to about 50 mg/kg, about 50 mg/kg to about 100 mg/kg, about 10 mg/kg to about 50 mg/kg, or about 10 mg/kg, about 25 mg/kg, about 50 mg/kg, about 75 mg/kg, about 100 mg/kg, or about 150 mg/kg, or a range from any one of the aforementioned values to any other of the aforementioned values. The compounds can also be administered to a subject to provide a steady-state plasma concentration of the drugs, alone or in combination, of about 1 μmol/L to about 25 μmol/L, or about 10 μmol/L, or about 15 μmol/L.

In some embodiments, the invention provides the compounds in effective concentrations at about 10 nM to about 100 μM. In another embodiment, the effective concentrations are from about 200 nM to about 50 μM, about 500 nM to about 40 μM, about 750 nM to about 25 μM, about 1 μM to about 20 μM, or about 1 μM to about 10 μM. In another embodiment, the effective concentration is considered to be a value such as a 50% activity concentration in a direct procaspase activation assay, in a cell apoptosis induction assay, or in an animal clinical therapeutic assessment. In one embodiment, such value is less than about 200 μM. In another embodiment, the value is less than about 10 μM but greater than about 10 nM. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The compounds described herein can be effective antitumor agents and have higher potency and/or reduced toxicity as compared to the administration of any single agent. The invention provides therapeutic methods of treating cancer in a mammal, which involve administering to a mammal having cancer an effective amount of a compound or composition described herein. A mammal includes a primate, human, rodent, canine, feline, bovine, ovine, equine, swine, caprine, bovine and the like. Cancer refers to any various type of malignant neoplasm, for example, colon cancer, breast cancer, melanoma and leukemia, among others described herein, and in general is characterized by an undesirable cellular proliferation, e.g., unregulated growth, lack of differentiation, local tissue invasion, and metastasis.

The ability of a compound of the invention to treat cancer may be determined by using assays well known to the art. For example, the design of treatment protocols, toxicity evaluation, data analysis, quantification of tumor cell kill, and the biological significance of the use of transplantable tumor screens are known. In addition, ability of a compound to treat cancer may be determined using the assays described above and in the citations and patent documents cited herein.

The invention also provides prodrug forms of compounds. Any compound that will be converted in vivo to provide PAC-1 or a compound of Formula I is a prodrug. Numerous methods of forming prodrugs are well known in the art. Examples of prodrugs and methods of preparing them are found, inter alia, in Design of Prodrugs, edited by H. Bundgaard, (Elsevier, 1985), Methods in Enzymology, Vol. 42, at pp. 309-396, edited by K. Widder, et. al. (Academic Press, 1985); A Textbook of Drug Design and Development, edited by Krosgaard-Larsen and H. Bundgaard, Chapter 5, "Design and Application of Prodrugs," by H. Bundgaard, at pp. 113-191, 1991); H. Bundgaard, Advanced Drug Delivery Reviews, Vol. 8, p. 1-38 (1992); H. Bundgaard, et al., *Journal of Pharmaceutical Sciences*, Vol. 77, p. 285 (1988); and Nogrady (1985) Medicinal Chemistry A Biochemical Approach, Oxford University Press, New York, pages 388-392).

Additionally, in some embodiments, PAC-1 can be exchanged for a PAC-1 derivative or other inhibitor, such as a compound described in U.S. Pat. No. 7,632,972 (Hergenrother et al.), U.S. Patent Publication Nos. 2012/0040995 (Hergenrother et al.) and 2007/0049602 (Hergenrother et al.), and U.S. application Ser. No. 12/597,287 (Hergenrother et al.). Useful compounds, methods, and techniques for cancer therapy that can be used in combination with the disclosure herein are described in the aforementioned documents, as well as in U.S. Pat. No. 6,303,329 (Heinrikson et al.), U.S. Pat. No. 6,403,765 (Alnemri), U.S. Pat. No. 6,878,743 (Choong et al.), and U.S. Pat. No. 7,041,784 (Wang et al.), and U.S. Patent Publication No. 2004/0180828 (Shi).

Methods for performing the tests and evaluating cancer cell lines can be carried out as described by Putt et al., *Nature Chemical Biology* 2006, 2(10), 543-550; Peterson et al., *J. Mol. Biol.* 2009, 388, 144-158; and Peterson et al., *Cancer Res.* 2010, 70(18), 7232-7241.

The following Example is intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1

Pharmaceutical Dosage Forms

The following formulations illustrate representative pharmaceutical dosage forms that may be used for the therapeutic or prophylactic administration of the combination compounds described herein, or pharmaceutically acceptable salts or solvates thereof (hereinafter referred to as 'Compounds X'):

|  | mg/tablet |
|---|---|
| (i) Tablet 1 | |
| 'Compounds X' | 200.0 |
| Lactose | 77.5 |
| Povidone | 15.0 |
| Croscarmellose sodium | 12.0 |
| Microcrystalline cellulose | 92.5 |
| Magnesium stearate | 3.0 |
|  | 400.0 |
| (ii) Tablet 2 | |
| 'Compounds X' | 120.0 |
| Microcrystalline cellulose | 410.0 |
| Starch | 50.0 |
| Sodium starch glycolate | 15.0 |
| Magnesium stearate | 5.0 |
|  | 600.0 |
| (iii) Capsule | mg/capsule |
| 'Compounds X' | 110.0 |
| Colloidal silicon dioxide | 1.5 |
| Lactose | 465.5 |
| Pregelatinized starch | 120.0 |
| Magnesium stearate | 3.0 |
|  | 700.0 |

|  | mg/mL |
|---|---|
| (iv) Injection 1 (1 mg/mL) | |
| 'Compounds X' | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |
| (V) Injection 2 (10 mg/mL) | |
| 'Compounds X' | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |
| (vi) Aerosol | mg/can |
| 'Compounds X' | 20 |
| Oleic acid | 10 |
| Trichloromonofluoromethane | 5,000 |
| Dichlorodifluoromethane | 10,000 |
| Dichlorotetrafluoroethane | 5,000 |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Compounds X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A composition comprising (a) a compound of Formula (I):

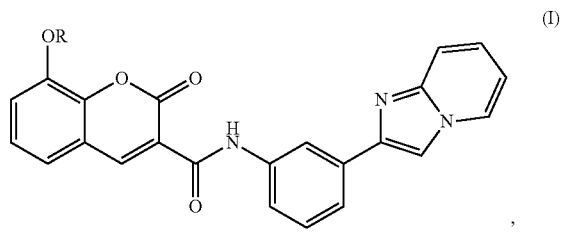

wherein R is H or Me;
(b) the compound PAC-1:

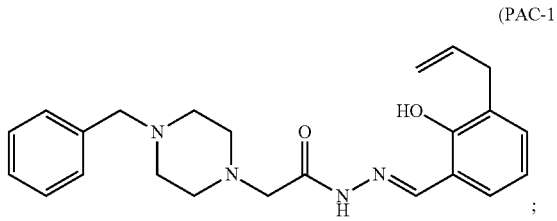

and (c) a pharmaceutically acceptable diluent, excipient, or carrier.

2. The composition of claim 1 wherein R of Formula (I) is H.

3. The composition of claim 1 wherein R of Formula (I) is Me.

4. The composition of claim 1 wherein the carrier comprises water and optionally a buffer, a cyclodextrin, or a combination thereof.

5. The composition of claim 4 wherein the carrier comprises a cyclodextrin wherein the cyclodextrin is 2-hydroxypropyl-β-cyclodextrin.

6. A method of inhibiting the growth or proliferation of cancer cells comprising contacting cancer cells with an effective amount of a composition of claim 1, thereby inhibiting the growth or proliferation of the cancer cells.

7. The method of claim 6 wherein the cancer cells are cells of anal cancer, bladder cancer, breast cancer, cervical cancer, colorectal cancer, gastric cancer, head and neck cancer, leukemia, lung cancer Hodgkin's lymphoma, Non-Hodgkin's lymphoma, malignant lymphoma, neuroblastomas, ophthalmic cancer, osteogenic carcinomas, ovarian cancer, prostate cancer, renal cancer melanoma, soft tissue sarcomas, thyroid cancer, or Wilms' tumor.

8. The method of claim 6 wherein the cancer cells are breast cancer cells, leukemia cells, or lymphoma cells.

9. A method of activating procaspase-3 to caspase-3 comprising contacting the procaspase-3 with a composition of claim 1.

10. The method of claim 9 wherein the contacting is in vitro.

11. The method of claim 9 wherein the contacting is in vivo.

12. A method of potentiating the activity of a compound of Formula (I):

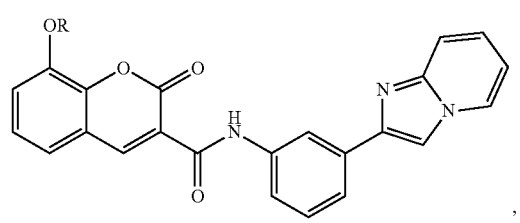

wherein R is H or Me;
comprising contacting a cancer cell with a combination of the compound of Formula I and an effective activating amount of PAC-1:

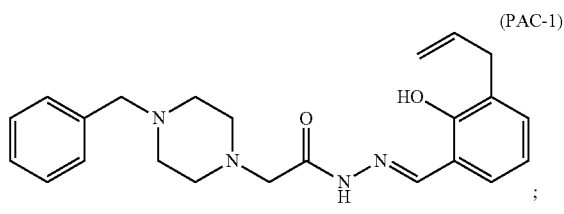 [SMILES: C=CCc1cccc(/C=N/NC(=O)CN2CCN(Cc3ccccc3)CC2)c1O]

wherein the PAC-1 potentiates the activity of the compound of Formula (I) toward the cancer cell.

13. A method of inducing apoptosis in a cancer cell comprising contacting the cancer cell with an effective amount of a compound of Formula (I):

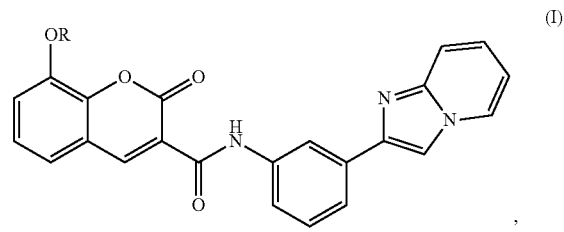

wherein R is H or Me;
and an effective amount of the compound PAC-1:

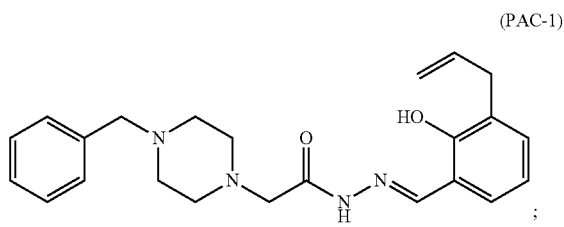 [SMILES: C=CCc1cccc(/C=N/NC(=O)CN2CCN(Cc3ccccc3)CC2)c1O]

wherein apoptosis is thereby induced in the cancer cell.

14. The method of claim 13 wherein the cancer cell is contacted with the compound of Formula (I) and the PAC-1 concurrently.

15. The method of claim 13 wherein the cancer cell is contacted with the compound of Formula (I) prior to contacting the cancer cell with PAC-1.

16. The method of claim 13 wherein the cancer cell is contacted with PAC-1 prior to contacting the cancer cell with the compound of Formula (I).

17. A method of inhibiting cancer, arresting cancer, relieving cancer, reversing the progression of cancer, reversing the severity of cancer, and/or therapeutically treating cancer, in a patient in need thereof comprising administering to the patient, concurrently or sequentially, a therapeutically effective amount of a compound of Formula (I):

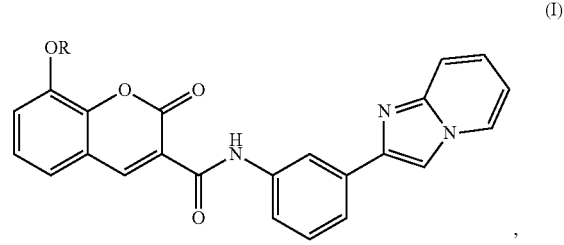

wherein R is H or Me;
and an effective amount of the compound PAC-1:

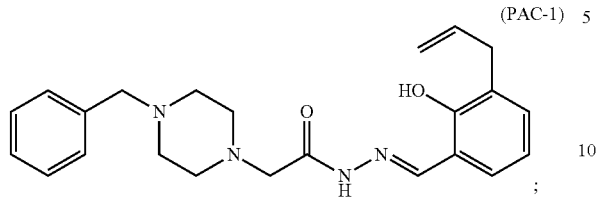

wherein the cancer is breast cancer, leukemia, or lymphoma.

18. The method of claim 17 wherein the compound of Formula (I) and the compound PAC-1 are administered concurrently.

19. The method of claim 17 wherein the compound of Formula (I) and the compound PAC-1 are administered sequentially.

20. The method of claim 19 wherein the compound of Formula (I) is administered before the compound PAC-1.

21. The method of claim 19 wherein the compound of Formula (I) is administered after the compound PAC-1.

* * * * *